US009248108B2

(12) United States Patent
Liu et al.

(10) Patent No.: US 9,248,108 B2
(45) Date of Patent: Feb. 2, 2016

(54) PUTRESCINE AND METHOD TO REDUCE RISK OF ANEUPLOID PREGNANCY

(71) Applicant: Ottawa Hospital Research Institute, Ottawa (CA)

(72) Inventors: Xingquan Johné Liu, Ottawa (CA); Yong Tao, Ottawa (CA)

(73) Assignee: OTTAWA HOSPITAL RESEARCH INSTITUTE, Ottawa (CA)

( * ) Notice: Subject to any disclaimer, the term of this patent is extended or adjusted under 35 U.S.C. 154(b) by 0 days.

(21) Appl. No.: 14/422,598

(22) PCT Filed: Aug. 21, 2013

(86) PCT No.: PCT/CA2013/050645
§ 371 (c)(1),
(2) Date: Feb. 19, 2015

(87) PCT Pub. No.: WO2014/029023
PCT Pub. Date: Feb. 27, 2014

(65) Prior Publication Data
US 2015/0224068 A1  Aug. 13, 2015

Related U.S. Application Data

(60) Provisional application No. 61/692,306, filed on Aug. 23, 2012.

(51) Int. Cl.
A61K 31/132 (2006.01)
(52) U.S. Cl.
CPC .................................... A61K 31/132 (2013.01)
(58) Field of Classification Search
CPC .................................................. A61K 31/132
See application file for complete search history.

(56) References Cited

PUBLICATIONS

Heby; "Putrescine, Spermidine and Spermine"; 1986; NIPS; 1:12-15.*
Tao et al.; "Deficiency of ovarian ornithine decarboxylase contributes to aging-related egg aneuploidy in mice"; Feb. 2013; Aging Cell; 12: 42-49.*
Liu et al.; "Peri-ovulatory putrescine to reduce aneuploidy conceptions"; Nov. 2012; Aging; 4(11): 723-725.*
Lefèevre et al.; "Polyamines on the Reproductive Landscape"; Oct. 2011; Endocrine Reviews; 32(5): 694-712.*
Tao et al., "Deficiency of ovarian ornithine decarboxylase contributes to aging-related egg aneuploidy in mice", Aging Cell, Feb. 2013, 12, 42-49, published online Nov. 26, 2012.
Liu et al., "Peri-ovulatory putrescine to reduce aneuploid conceptions", Aging, Nov. 2012, 4(11), 723-725.
Pendeville et al., "The ornithine decarboxylase gene is essential for cell survival during early murine development", Molecular and Cellular Biology, Oct. 2001, 21(19), 6549-6558.
Macrae et al., "Developmental effect of polyamine depletion in Caenorhabditis elegans", Biochemical Journal, 1998, 333, 309-315.
Jiang et al., "Ornithine decarboxylase gene deletion mutants of Leishmania donovani", The Journal of Biological Chemistry, 1999, 274(6), 3781-3788.
Zhou et al., "Antiapoptotic role for ornithine decarboxylase during oocyte maturation", Molecular and Cellular Biology, Apr. 2009, 29(7), 1786-1795.
Lefevre et al., "Polyamines on the reproductive landscape", Endocrine Reviews, Oct. 2011, 32(5), 694-712.
International Search Report and Written Opinion for corresponding International Application No. PCT/CA2013/050645 dated Nov. 4, 2013.
Angell R (1997). First-meiotic-division nondisjunction in human oocytes. Am. J. Hum. Genet. 61, 23-32.
Angell RR (1991). Predivision in human oocytes at meiosis I: a mechanism for trisomy formation in man. Hum. Genet. 86, 383-387.
Baird DT, Collins J, Egozcue J, Evers LH, Gianaroli L, Leridon H, Sunde A, Templeton A, Van SA, Cohen J, Crosignani PG, Devroey P, Diedrich K, Fauser BC, Fraser L, Glasier A, Liebaers I, Mautone G, Penney G, Tarlatzis B (2005). Fertility and ageing. Hum. Reprod. Update. 11, 261-276.
Bastida CM, Cremades A, Castells MT, Lopez-Contreras AJ, Lopez-Garcia C, Tejada F, Penafiel R (2005). Influence of ovarian ornithine decarboxylase in folliculogenesis and luteinization. Endocrinology 146, 666-674.
Chard, T (1991) Frequency of implantation and early pregnancy loss in natural cycles. Baillieres Clin. Obstet. Gynaecol. 5, 179-189.
Chiang T, Duncan FE, Schindler K, Schultz RM, Lampson MA (2010). Evidence that weakened centromere cohesion is a leading cause of age-related aneuploidy in oocytes. Curr. Biol. 20, 1522-1528.
Dailey T, Dale B, Cohen J, Munne S (1996). Association between nondisjunction and maternal age in meiosis-II human oocytes. Am. J. Hum. Genet. 59, 176-184.
Duncan FE, Chiang T, Schultz RM, Lampson MA (2009). Evidence that a defective spindle assembly checkpoint is not the primary cause of maternal age-associated aneuploidy in mouse eggs. Biol. Reprod. 81, 768-776.
Fozard JR, Part ML, Prakash NJ, Grove J, Schechter PJ, Sjoerdsma A, Koch-Weser J (1980a). L-Ornithine decarboxylase: an essential role in early mammalian embryogenesis. Science 208, 505-508.
Fozard JR, Prakash NJ, Grove J (1980b). Ovarian function in the rat following irreversible inhibition of L-ornithine decarboxylase. Life Sci. 27, 2277-2283.
Garcia-Faroldi G, Correa-Fiz F, Abrighach H, Berdasco M, Fraga MF, Esteller M, Urdiales JL, Sanchez-Jimenez F, Fajardo I (2009). Polyamines affect histamine synthesis during early stages of IL-3-induced bone marrow cell differentiation. J. Cell Biochem. 108, 261-271.
Goudlin RC (1965). Non-disjunction and maternal age in the mouse. J. Reprod. Fertil. 9, 355-356. Hassold T, Hunt P (2001). To err (meiotically) is human: the genesis of human aneuploidy. Nat. Rev. Genet. 2, 280-291.

(Continued)

Primary Examiner — Timothy Thomas
(74) Attorney, Agent, or Firm — David Nauman; Borden Ladner Gervais LLP

(57) ABSTRACT

A medicament for reducing the risk of having an aneuploid pregnancy in a woman with reduced ovarian ornithine decarboxylase (ODC) activity level, the medicament includes putrescine. A use of putrescine for reducing the risk of having an aneuploid pregnancy in a woman with reduced ovarian ODC activity levels. A method for reducing the risk of having an aneuploid pregnancy in a woman with reduced ovarian ODC activity levels by administering putrescine.

20 Claims, 6 Drawing Sheets

(56) References Cited

PUBLICATIONS

Hodges CA, Hunt PA (2002). Simultaneous analysis of chromosomes and chromosome-associated proteins in mammalian oocytes and embryos. Chromosoma 111, 165-169.

Icekson I, Kaye AM, Lieberman ME, Lamprecht SA, Lahav M, Lindner HR (1974). Stimulation by luteinizing hormone of ornithine decarboxylase in rat ovary: preferential response by follicular tissue. J. Endocrinol. 63, 417-418.

Kobayashi Y, Kupelian J, Maudsley DV (1971). Ornithine decarboxylase stimulation in rat ovary by luteinizing hormone. Science 172, 379-380.

Koehler KE, Schrump SE, Cherry JP, Hassold TJ, Hunt PA (2006). Near-human aneuploidy levels in female mice with homeologous chromosomes. Curr. Biol. 16, R579-R580.

Kuliev A, Zlatopolsky Z, Kirillova I, Spivakova J, Cieslak JJ (2011). Meiosis errors in over 20,000 oocytes studied in the practice of preimplantation aneuploidy testing. Reprod. Biomed. Online. 22, 2-8.

Lister LM, Kouznetsova A, Hyslop LA, Kalleas D, Pace SL, Barel JC, Nathan A, Floros V, Adelfalk C, Watanabe Y, Jessberger R, Kirkwood TB, Hoog C, Herbert M (2010). Age-related meiotic segregation errors in Mammalian oocytes are preceded by depletion of cohesin and Sgo2. Curr. Biol. 20, 1511-1521.

Mahmood R, Brierley CH, Faed MJ, Mills JA, Delhanty JD (2000). Mechanisms of maternal aneuploidy: FISH analysis of oocytes and polar bodies in patients undergoing assisted conception. Hum. Genet. 106, 620-626.

Merriman JA, Jennings PC, McLaughlin EA, Jones KT (2012). Effect of aging on superovulation efficiency, aneuploidy rates, and sister chromatid cohesion in mice aged up to 15 months. Biol. Reprod. 86, 49.

Metcalf BW, Bey P, Danzin C, Jung MJ, Casara P, Vevert JP (1978). Catalytic irreversible inhibition of mammalian ornithine decarboxylase (E.C.4.1.1.17) by substrate and product analogues. J. Am. Chem. Soc. 100, 2551-2553.

Nilsson JA, Keller UB, Baudino TA, Yang C, Norton S, Old JA, Nilsson LM, Neale G, Kramer DL, Porter CW, Cleveland JL (2005). Targeting ornithine decarboxylase in Myc-induced lymphomagenesis prevents tumor formation. Cancer Cell 7, 433-444.

Pan, H, Ma, P, Zhu, W, Schultz, RM (2008). Age-associated increase in aneuploidy and changes in gene expression in mouse eggs. Dev. Biol. 316, 397-407.

Pegg AE (2006). Regulation of ornithine decarboxylase. J. Biol. Chem. 281, 14529-14532.

Poulin R, Lu L, Ackermann B, Bey P, Pegg AE (1992). Mechanism of the irreversible inactivation of mouse ornithine decarboxylase by α-difluoromethylornithine. Characterization of sequences at the inhibitor and coenzyme binding sites. J. Biol. Chem. 267, 150-158.

Selesniemi K, Lee HJ, Muhlhauser A, Tilly JL (2011). From the Cover: Prevention of maternal aging-associated oocyte aneuploidy and meiotic spindle defects in mice by dietary and genetic strategies. Proc. Natl. Acad. Sci. U. S. A 108, 12319-12324.

Sunkara PS, Wright DA, Nishioka K (1981). An essential role for putrescine biosynthesis during meiotic maturation of amphibian oocytes. Dev. Biol. 87, 351-355.

Whitney PA, Morris DR (1978). Polyamine auxotrophs of *Saccharomyces cerevisiae*. J. Bacteriol. 134, 214-220.

Wolstenholme J, Angell RR (2000). Maternal age and trisomy—a unifying mechanism of formation. Chromosoma 109, 435-438.

Younglai EV, Godeau F, Mester J, Baulieu EE (1980). Increased ornithine decarboxylase activity during meiotic maturation in Xenopus laevis oocytes. Biochem. Biophys. Res. Commun. 96, 1274-1281.

Angell RR, Xian J, Keith J, Ledger W, Baird DT (1994). First meiotic division abnormalities in human oocytes: mechanism of trisomy formation. Cytogenet. Cell Genet. 65, 194-202.

Evans,E.P. (1987). Karyotying and sexing of gametes, embryos and fetuses and in situ hybridization to chromosomes. In Mammalian Development: a practical approachl , M.Monk, ed. (Washington DC: IRL Press), p. 263.

\* cited by examiner

PUTRESCINE AND METHOD TO REDUCE RISK OF ANEUPLOID PREGNANCY

CROSS REFERENCE TO RELATED APPLICATIONS

This application is a U.S. National Entry of PCT patent application Ser. No. PCT/CA2013/050645, filed Aug.21, 2013, claims the benefit of priority of U.S. Provisional Application Ser. No. 61/692,306, filed Aug. 23, 2012, which are incorporated herein by reference.

FIELD

The present disclosure relates to putrescine and its use in reducing the risk of aneuploid pregnancy.

BACKGROUND

It is estimated that 10-30% of fertilized human eggs are aneuploid. Most of these aneuploid fertilizations result in either embryo demise prior to clinical recognition of pregnancy, or miscarriages. Aneuploidy is also the single most important contributing factor in severe birth defects (e.g. Down syndrome). The majority (>80%) of embryo aneuploidies are of maternal origin (eggs having incorrect number of chromosomes), with majority being due to premature separation of sister chromatids (PSSC) immediately prior to ovulation. Advanced maternal age is the most important contributing factor of aneuploidy, with women over 32 having a rapidly increasing risk of carrying a trisomy pregnancy, where the risk reaches over 30% by age 40 (Hassold and Hunt, 2001).

In order to avoid aneuploid pregnancies, women undergoing in vitro fertilization (IVF) may undertake pre-implantation genetic diagnosis (PIGD), which involves polar body or embryo biopsy. This procedure is invasive and therefore inherently harmful to the implanting embryos. Overall, the benefit is not universally recognized. Several major public health authorities have issued strong warnings against its use, and it is prohibited in some countries (for example, Germany).

It is, therefore, desirable to provide a way to reduce the risk of having an aneuploid pregnancy.

SUMMARY

It is an object of the present disclosure to reduce the risk of having an aneuploid pregnancy.

According to one aspect, there is provided a medicament for reducing the risk of having an aneuploid pregnancy in a human female with reduced ovarian ornithine decarboxylase (ODC) activity level. The medicament includes: putrescine; and a pharmacologically acceptable excipient, diluent or carrier.

The human female with reduced ovarian ODC activity level may be a human female older than 32 years of age.

The putrescine may be formulated for administration at about 0.02 g/kg to about 1 g/kg daily.

The medicament may be formulated for administration of putrescine at least on the day of ovulation. In one example, the medicament may be formulated for administration of putrescine up to and including the day of ovulation, such as for one week up to and including the day of ovulation. In another example, the human female maybe an IVF patient and the medicament may be formulated for administration of putrescine to the IVF patient for one week up to the morning of egg retrieval. In yet another example, the medicament may be formulated for administration of putrescine for 5-8 days up to and including the day of conception.

The medicament may be formulated for oral or subcutaneous administration, for example subcutaneous or intravenous injection.

According to another aspect, there is provided a use of putrescine for reducing the risk of having an aneuploid pregnancy in a human female with reduced ovarian ODC activity level. The human female with reduced ovarian ODC activity level may be a human female older than 32 years of age.

The putrescine may be formulated for administration at about 0.02 g/kg to about 1 g/kg daily.

The putrescine may be formulated for administration at least on the day of ovulation. In one example, the putrescine may be formulated for administration up to and including the day of ovulation, such as for one week up to and including the day of ovulation. In another example, the human female maybe an IVF patient and the putrescine may be formulated for administration to the IVF patient for one week up to the morning of egg retrieval. In yet another example, the putrescine may be formulated for administration for 5-8 days up to and including the day of conception.

Reducing the risk of having an aneuploid pregnancy may include reducing the ovulation of aneuploid eggs and/or reducing the generation of aneuploid embryos.

Reducing the risk of having an aneuploid pregnancy may include: increasing the probability that the human female will have a viable pregnancy, reducing the probability that the human female will have a child with a birth defect, or both, when compared to the probability when the human female is not administered the putrescine.

According to another aspect, there is provided a method of reducing the risk of having an aneuploid pregnancy in a human female with reduced ovarian ODC activity level. The method includes administering putrescine to a peri-ovulatory human female.

The human female with reduced ovarian ODC activity level may be a human female older than 32 years of age.

The putrescine may be administered to the human female at about 0.02 g/kg to about 1 g/kg daily.

The putrescine may be administered at least on the day of ovulation. In one example, the putrescine may be administered up to and including the day of ovulation, such as for one week up to and including the day of ovulation. In another example, the human female maybe an IVF patient and the putrescine may be administered to the IVF patient for one week up to the morning of egg retrieval. In yet another example, the putrescine may be administered for 5-8 days up to and including the day of conception.

Reducing the risk of having an aneuploid pregnancy may include reducing the ovulation of aneuploid eggs and/or reducing the generation of aneuploid embryos.

Reducing the risk of having an aneuploid pregnancy may include: increasing the probability that the human female will have a viable pregnancy, reducing the probability that the human female will have a child with a birth defect, or both, when compared to the probability when the human female is not administered the putrescine.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

FIG. 2 also shows a graph illustrating ODC activity expressed as nmol $CO_2$ released per hour per gram of ovarian tissues.

DETAILED DESCRIPTION

Figure 1:
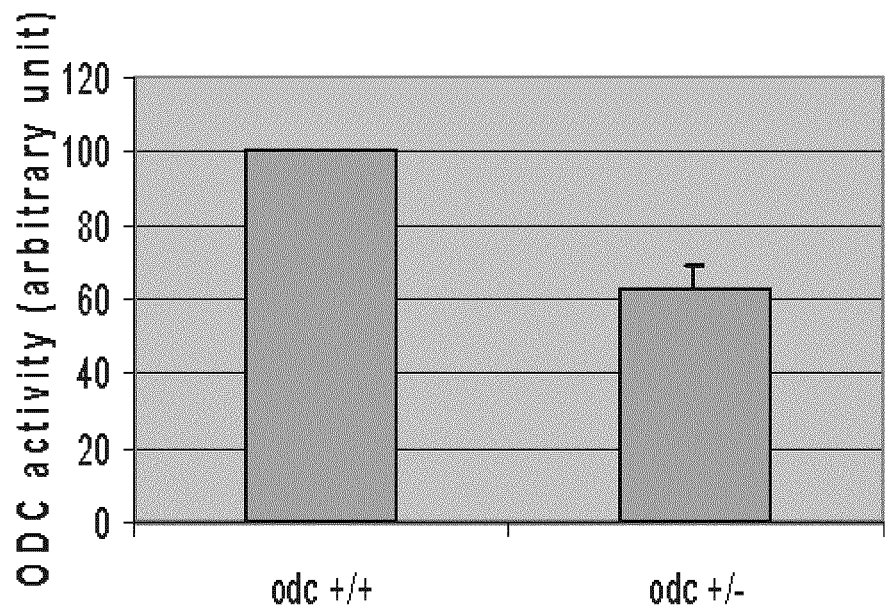
FIG. 1 is a graph illustrating ovarian ODC activity of 8-week-old odc+/− compared to the wild-type littermate. Shown are means (with standard deviations) of three independent experiments, each with wild-type mice set at 100 a.u. (arbitrary units).

It has been known for more than four decades that during mammalian estrous cycles, luteinizing hormone stimulates a transitory rise in the ovaries of ODC activity and its enzymatic product putrescine, concurrent with oocyte maturation in vivo. Since ODC inhibition was previously shown to result in normal gestation, inhibition of this transitory ODC/putrescine rise was previously believed to not affect oocyte maturation or ovulation.

Using several mouse models and combining in vitro and in vivo approaches, the authors of the present disclosure have now found that deficiency of ODC during oocyte maturation is correlated with increased levels of egg aneuploidies. The authors additionally believe that the transitory ovarian ODC rise in late proestrus is important for ensuring proper chromosome segregation during oocyte maturation. Therefore, the authors believe that inhibition of the transitory ovarian ODC activity rise increases aneuploidies in ovulated eggs and in 2-cell embryos.

ODC catalyzes the conversion of ornithine to putrescine, releasing $CO_2$. The authors of the present disclosure now believe that the deficiency in putrescine production is at least one factor in the increase in aneuploid pregnancy.

In view of the findings discussed herein, the present disclosure generally provides: (a) a medicament for reducing the risk of having an aneuploid pregnancy in a woman with reduced ovarian ODC activity level, the medicament includes putrescine; (b) a use of putrescine for reducing the risk of having an aneuploid pregnancy in a woman with reduced ovarian ODC activity levels; and (c) a method for reducing the risk of having an aneuploid pregnancy in a woman with reduced ovarian ODC activity levels by administering putrescine. In the current disclosure, "human female" and "woman" are used interchangeably.

One (1) g of putrescine is 11.4 mmol, or 228 nmol per g tissue for a 50 kg women, if the putrescine is administered at one time and evenly distributed throughout her body. The transitory ovarian putrescine concentrations have been determined to peak at 160 nmol per g ovarian tissues in one study (Bastida et al. 2005) and 250 nmol per g ovarian tissue in another (Fozard et al. 1980b). In the oral putrescine supplementation experiments described below, no difference was observed in the amount of water or "putrescine water" consumed by the respective animals. Assuming that the daily intake of water is equivalent to 10% of their body weight, the daily putrescine intake in the experiments is approximately 1 g per kg body weight, or 6.2 μmol putrescine (molecular weight of putrescine hydrochloride is 161) per g body weight. However, because mice drink water very frequently and because exogenous putrescine clears out very rapidly, the steady-state putrescine levels in these mice are much lower at any given time.

The putrescine may be formulated for administration to a human female with reduced ovarian ODC activity levels at about 0.02 g/kg to about 1 g/kg daily. The putrescine may be formulated for administration to a human female with reduced ovarian ODC activity levels at more than about 1 g/kg daily. The dose of putrescine may be administered, for example: in a single dose once a day, in multiple smaller doses a number of times per day, or via a constant administration over the course of a certain time period. Constant administration may be achieved, for example, by administration of a sustained release formulation that includes the putrescine, or by continuous or repeated subcutaneous administration over a certain time period. Subcutaneous administration may include, for example, intravenous injection or subcutaneous injection. One particular example of subcutaneous injection includes continuous subcutaneous infusion of putrescine, similar to the manner in which insulin is administered by an insulin pump.

Women with reduced ovarian ODC activity levels may be women older than 32 years of age. After this age, it has been shown that the incidence of trisomy increases exponentially (Hassold, T. & Hunt, P. To err (meiotically) is human: the genesis of human aneuploidy. Nat. Rev. Genet. 2001 2, 280-291). The mouse studies disclosed herein (e.g. FIG. 2), as well as unpublished mouse studies, indicate a strong correlation between aging and ovarian ODC levels, with greater than 50% reduction in ODC levels by 6 months of age. Considering that lab mice live at least 2 years, the authors of the present disclosure believe that that human women also exhibit significant reduction of ovarian ODC levels at a relatively young age, for example at 32 years of age.

The putrescine may be formulated for administration at least on the day of ovulation. In some examples, the putrescine may be formulated for administration for one week up to and including the day of ovulation. In other examples, the putrescine may be formulated for administration for one week up to the morning of egg retrieval for IVF patients. In yet another example, the putrescine may be formulated for administration 5-8 days up to and including the day of conception.

The putrescine may be administered in any manner that results in a plasma concentration of putrescine that reduces the risk of aneuploid pregnancy. For example, the administration may be enteral, topical, or parenteral. Enteral administration may be, for example, by ingestion of a pharmaceutical medicament or dietary supplement that contains the putrescine. Parenteral administration may be, for example, intravenous or subcutaneous injection of a pharmaceutical composition that contains the putrescine. The putrescine may be formulated for delivery to the ovaries, oocytes or both.

As discussed above, aneuploid fertilizations often result in either embryo demise prior to clinical recognition of pregnancy, or miscarriages. Aneuploidy is also a contributing factor in severe birth defects. Reducing the risk of having an aneuploid pregnancy may: increase the possibility of having a viable pregnancy, reduce the possibility of having a child with a birth defect, or both.

The risk of having an aneuploid pregnancy in women with reduced ovarian ODC activity levels may be reduced by reducing the ovulation of aneuploid eggs, thereby reducing the generation of aneuploid embryos. Women with reduced ovarian ODC activity levels may be women older than 32 years of age. In such women, reducing the risk of having an aneuploid pregnancy may improve the fertility of women, for example by increasing the possibility that a woman will become pregnant and carry the pregnancy to term.

Ornithine Decarboxylase and Female Reproduction

ODC is an essential enzyme in all eukaryotes, from yeasts (Whitney & Morris, 1978) to mammals (Pendeville et al., 2001), due to its role in cell replication. Consistent with this role, during mouse embryogenesis ODC expression increases sharply after implantation (E6-E8), at a time of rapid cell proliferation (Fozard et al., 1980a). Chemical inhibition (Fozard et al., 1980a) or gene knockout (Pendeville et al., 2001) invariably causes embryonic death at this period.

On the other hand, the function of ODC during mammalian ovulation remains enigmatic (Lefevre et al., 2011). During estrous cycles in rats (Kobayashi et al., 1971) and mice (Bastida et al., 2005), ovarian ODC activity, and the corresponding ovarian putrescine concentration (Fozard et al., 1980b; Bastida et al., 2005) exhibit a luteinizing hormone (LH) mediated transitory rise during the evening of proestrus, concurrent with oocyte maturation in vivo. This level of ODC activity is at least 10 times that required for the preceding follicular phase, which is characterized by significant cell proliferation within the antral follicles (Bastida et al., 2005; Fozard et al., 1980b; Kobayashi et al., 1971), suggesting a function(s) unrelated to cell proliferation.

Within the ovaries, LH stimulates the transitory rise of ODC protein mainly in preovulatory follicles (Icekson et al., 1974), both in the somatic (theca and granulosa) cells and in the oocytes (Bastida et al., 2005). However, complete inhibition of this transitory ODC/putrescine rise does not affect ovulation (Fozard et al., 1980b; Bastida et al., 2005). It has been suggested that the transitory rise of ovarian ODC activity is required for luteinization of the granulosa cells to produce progesterone (Bastida et al., 2005), although gestation appears normal when the transitory ODC/putrescine rise is inhibited (Fozard et al., 1980b). Similarly, oocyte maturation in Xenopus laevis, a species lacking luteinzation or implantation, is also accompanied by similarly significant and transitory rise in ODC activity (Younglai et al., 1980; Sunkara et al., 1981; Zhou et al., 2009). ODC activity rise during frog oocyte maturation has been shown to be due to de novo protein translation and that its complete inhibition, although not affecting polar body emission, leads to increase of oxidative stress and apoptosis (Zhou et al., 2009).

Since ODC inhibition was previously shown to result in normal gestation, it was previously believed that ODC enzyme activity did not affect oocyte maturation or ovulation.

EXAMPLE 1

Inhibition of ODC and Oocyte Maturation in Vitro

To determine if inhibition of oocyte ODC activity affects mouse oocyte in vitro maturation (IVM), DFMO, an enzyme-activated irreversible inhibitor for eukaryotic ODC (Metcalf et al., 1978; Poulin et al., 1992; Pegg, 2006) was employed. Immature mouse oocytes (a.k.a. "GV oocytes" for the presence of intact germinal vesicle) from young CF1 mice (7-8 weeks of age) were cultured in medium (control) or medium containing 5 mM DFMO (Garcia-Faroldi et al., 2009).

DFMO in oocyte IVM medium did not affect spindle assembly or first polar body emission (776/945 or 82%, compared with 676/843 or 80.2% for control), consistent with observation in frog oocytes (Zhou et al., 2009).

All metaphase II eggs were subjected to karyotype analyses and counted spreads that contained 18 or more chromosomes and in which all chromosomes were close together, to eliminate over-spread karyotypes. Only hyperploid eggs, those containing 21 or more chromosomes, were considered aneuploid, to avoid artifacts due to loss of chromosomes during preparation of chromosome spreads (Koehler et al., 2006). In this set of experiments, in which only DNA staining was employed, hyperploid oocytes that contained extra whole chromosomes (dyads) were not distinguished from those that contained separated sister(s), because it is often difficult to differentiate a small chromosome dyad and a single sister in telocentric chromosomes such as in mouse. Nonetheless these results indicated a significant increase of aneuploidies in oocytes treated with DFMO during in vitro maturation (Table 1 and Table 2, below).

| Treatment | N (cells) | Hypoploid 18 | Hypoploid 19 | Euploid 20 | Hyperploid 21 | Hyperploid 22 | % Hyperploidy |
|---|---|---|---|---|---|---|---|
| Control | 287 | 10 | 23 | 251 | 3 | 0 | 1.0 |
| DFMO | 205 | 2 | 18 | 175 | 10 | 0 | 4.9 * |
| DFMO + Put | 95 | 1 | 16 | 76 | 2 | 0 | 2.1 ** |

\* P = 0.0186 compared to control
\*\* P = 0.6014 compared to Control;
\*\* P = 0.3509 compared to DFMO Table 1 DFMO increases aneuploidy rate of young CF1 mice in vitro. GV oocytes from 7-8-week-old CF1 mice were incubated for 17 h in αMEM (control), αMEM with 5 mM DFMO, or αMEM with 5 mM DFMO together with 5 mM putrescine. Metaphase II eggs were karyotyped with chromosome staining only. N: total number of interpretable metaphase II spreads, with 18 or more chromosomes. Hypoploid: 18-19 chromosomes. Euploid: 20 chromosomes. Hyperploid: 21 chromosomes. Detailed breakdowns are available in Table 2.

| Treatment | Date | N | Hypoploid | Euploid | Hyperploid |
|---|---|---|---|---|---|
| Control | Sep. 22, 2009 | 25 | 6 (19, 4×; 18, 2×) | 19 | 0 |
|  | Sep. 24, 2009 | 24 | 0 | 23 | 1 (21) |
|  | Sep. 25, 2009 | 46 | 3 (19; 19; 18) | 42 | 1 (21) |
|  | Nov. 2, 2009 | 45 | 5 (19, 4×; 18) | 40 | 0 |

-continued

| Treatment | Date | N | Hypoploid | Euploid | Hyperploid |
|---|---|---|---|---|---|
| | Nov. 3, 2009 | 4 | 1 (19) | 3 | 0 |
| | Nov. 4, 2009 | 50 | 5 (19, 3×; 18; 18) | 45 | 0 |
| | Nov. 18, 2009 | 37 | 4 (19, 3×; 18) | 33 | 0 |
| | Nov. 20, 2009 | 55 | 9 (19, 6×; 18, 3×) | 46 | 1 (21) |
| DFMO | Oct. 6, 2009 | 56 | 4 (19, 4×) | 48 | 4 (21, 4×) |
| | Nov. 5, 2009 | 22 | 2 (19; 18) | 18 | 2 (21, 2×) |
| | Nov. 12, 2009 | 51 | 3 (19, 3×) | 47 | 1 (21) |
| | Nov. 13, 2009 | 2 | 1 (19) | 0 | 1 (21) |
| | Nov. 14, 2009 | 20 | 3 (19, 3×) | 17 | 0 |
| | Nov. 16, 2009 | 23 | 1 (19) | 21 | 1 (21) |
| | Nov. 22, 2009 | 31 | 6 (19, 5×; 18) | 24 | 1 (21) |
| DFMO + Putrescine | Oct. 7, 2009 | 40 | 3 (19, 3×) | 36 | 1 (21) |
| | Oct. 21, 2009 | 23 | 2 (19, 2×) | 21 | 0 |
| | Oct. 27, 2009 | 32 | 12 (19, 11×; 18) | 19 | 1 (21) |
| | Oct. 28, 2009 | 0 | 0 | 0 | 0 |

Table 2 Detailed breakdown of data listed in Table 1 (DFMO in vitro). N: number of interpretable MII spreads with 18 or more chromosomes. "19, 4×": four oocytes each with 19 chromosomes.

Rescue experiments in which 5 mM putrescine was added together with DFMO to the IVM medium were carried out to confirm the specificity of DFMO in ODC inhibition. Analysis of a relatively small number of oocytes suggested that putrescine supplementation reduced egg aneuploidies caused by DFMO (Table 1 and Table 2).

EXAMPLE 2

Inhibition of ODC and Oocyte Maturation In Vivo

Figure 2:
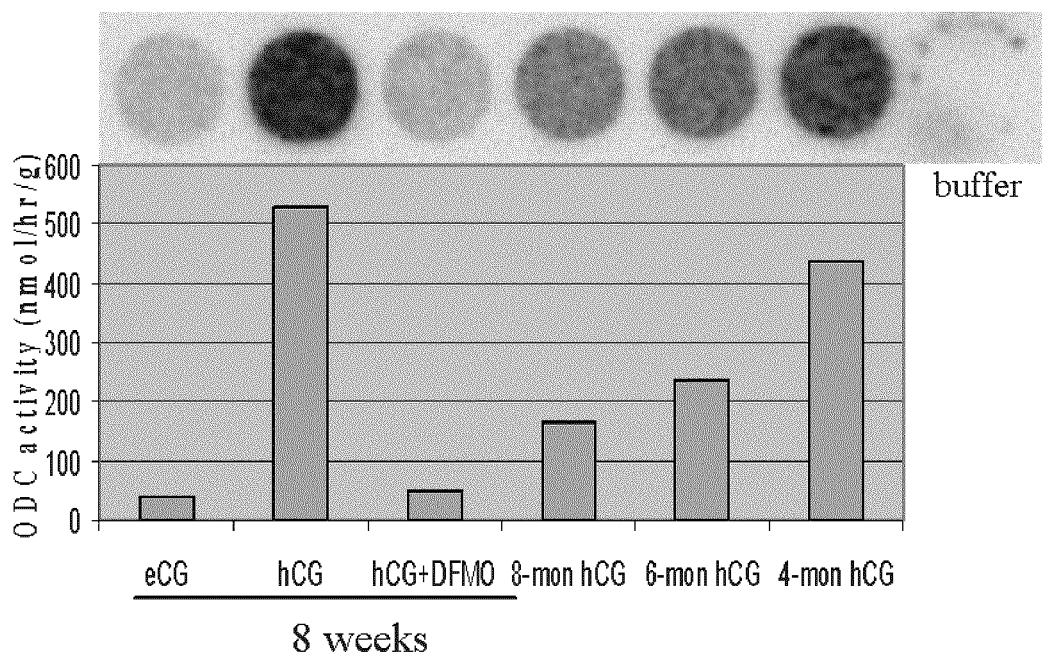
FIG. 2 shows a representative (C57BL/6) ovarian ODC activity assay, with 2 mg of ovarian tissues in each sample. Shown on top is the image generated from scanning the Storage phosphor screen that had been exposed to the $Ba^{14}CO_3$ reaction strip. The far right well contained ovarian extraction buffer as negative control.
Figure 3:
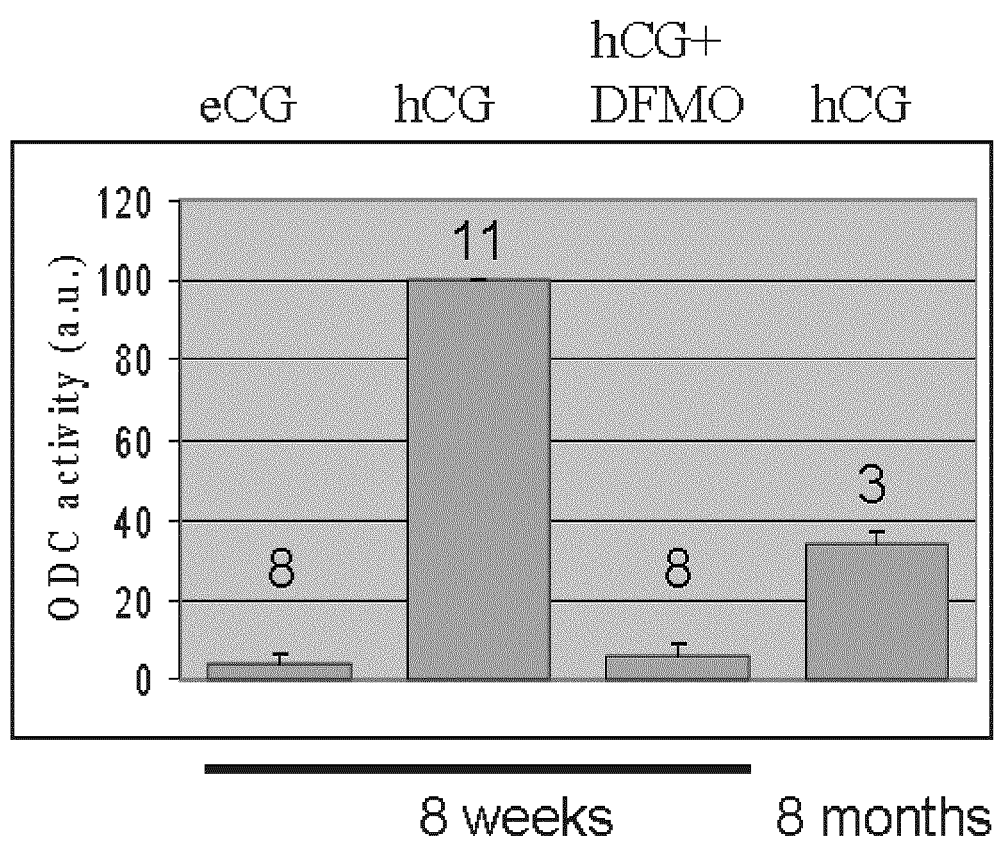
FIG. 3 is a graph illustrating ovarian ODC activity, in arbitrary units relative to hCG-stimulated young (8-weekold) C57BL/6 mice (set at 100), of eCG-primed young C57BL/6 mice, hCG-stimulated young C57BL/6 mice, hCG-stimulated young C57BL/6 mice with 48 h α-difluoromethylornithine (DFMO) in drinking water, and hCG-stimulated old (8 months) C57BL/6 mice. Shown are means with standard deviations of 3-11 determinations (indicated), each with a different mouse.
Figure 4:
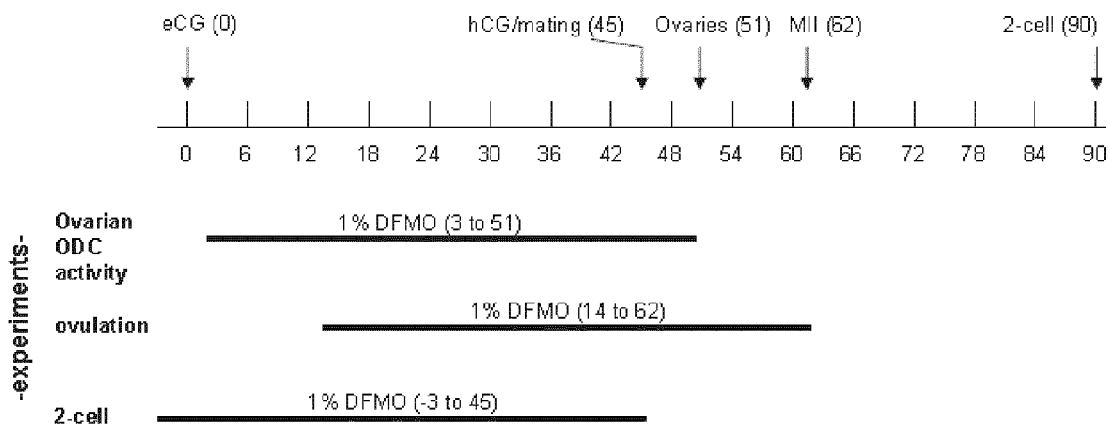
FIG. 4 illustrates DFMO drinking water schedules. Timelines (hours, time of eCG injection set as 0) of the 48 h DFMO in mouse drinking water (1%) relative to hormonal treatments and mouse sacrifice in the various experiments.

The effect of DFMO on egg aneuploidy in vivo was also examined. It was first confirmed that DFMO in mouse drinking water (Nilsson et al., 2005) (1%; see FIG. 4 for details) efficiently inhibited the ovarian ODC activity in young mice (FIG. 2, 3, compare "hCG+DFMO" to "hCG" in 8-week-old mice). Oviduct-derived metaphase II eggs, from control mice and DFMO treated mice, were subjected to karyotype analyses. In these and all subsequent egg karyotype analyses, anti-CREST antibodies were used to label centromeres (Hodges & Hunt, 2002), in addition to DNA staining. This modification allowed unambiguous identification of single sister chromatid(s) in metaphase II eggs, termed premature separation of sister chromatids (PSSC), the predominant form of mouse egg aneuploidies found in this study (see Table 3).

| phenotype | frequency | phenotype | frequency | phenotype | frequency |
|---|---|---|---|---|---|
| Euploid (72.7%) | | | | PSSC (5.7%) | |
| 20 | 1041 | 20 + 0.5 × 2 | 2 | 18 + 0.5 × 2 | 5 |
| Hyperploid (0.70%) | | 20 + 0.5 × 1 | 19 | 18 + 0.5 × 1 | 5 |
| 22 | 1 | 19 + 0.5 × 3 | 1 | 17 + 0.5 × 5 | 1 |
| 21 | 9 | 19 + 0.5 × 2 | 15 | 17 + 0.5 × 4 | 1 |
| Hypoploid (20.9%) | | 19 + 0.5 × 1 | 20 | 17 + 0.5 × 3 | 1 |
| 19 | 220 | 18 + 0.5 × 4 | 2 | 17 + 0.5 × 2 | 6 |
| 18 | 80 | 18 + 0.5 × 3 | 2 | 16 + 0.5 × 6 | 1 |

N = 1432

Table 3 Summary of all karyotypes shown in Table 4, Table 6, Table 8 and Table 13 PSSC (5.7%) is much more prevalent than whole chromosome nondisjunction, estimated by hyperploidies (0.7%), in mouse oocytes.

| Treatment | N (cells) | Hypoploid 18 | Hypoploid 19 | Euploid 20 | Hyperploid 21 | Hyperploid 22 | PSSC | % Hyperploidy | % Aneuploidy |
|---|---|---|---|---|---|---|---|---|---|
| odc WT | 149 | 15 | 42 | 91 | 0 | 0 | 1 | 0 | 0.7 |
| odc Het | 127 | 13 | 23 | 87 | 0 | 0 | 4 | 0 | 3.1 * |

* P = 0.1839

Table 4 Heterozygous odc mice exhibits a slight increase of egg aneuploidy rate in vivo. Young (7-8 weeks) odc+/− and odc+/+ mice were superovulated. Oviduct-derived metaphase II eggs were karyotyped by dual stains (anti-CREST and Sytox green) of metaphase II chromosomes. N: number of interpretable metaphase II karyotypes containing at least 18 dyads or the equivalent (e.g. 17 dyads plus 2 separated sister chromatids). Hypoploid: 18-19 dyads. Euploid: 20 dyads. Hyperploid: 21 or 22 dyads. PSSC: any karyotypes containing separated sister chromatid(s), with the total of at least 18 dyads or the equivalents. Aneuploid: 2×hyperploid+PSSC. Detailed breakdown are in Table 5.

| Genotype | Date | Countable | Euploid | Hyperploid | Hypoploid | PSSC |
|---|---|---|---|---|---|---|
| odc +/− het | Feb. 23, 2011 | 44 | 31 | 0 | 12 (19, 8×; 18, 4×) | 1 (17 + 0.5 × 2) |

-continued

| Genotype | Date | Countable | Euploid | Hyperploid | Hypoploid | PSSC |
|---|---|---|---|---|---|---|
| odc +/+ wt | Feb. 10, 2011 | 2 | 1 | 0 | 1 (19) | 0 |
| odc +/− het | Feb. 10, 2011 | 12 | 10 | 0 | 2 (18; 18) | 0 |
| odc +/+ wt | Feb. 4, 2011 | 5 | 4 | 0 | 1 (19) | 0 |
| odc +/− het | Feb. 4, 2011 | 4 | 2 | 0 | 2 (19; 18) | 0 |
| odc +/+ wt | Jan. 18, 2011 | 21 | 13 | 0 | 8 (19, 6×; 18, 2×) | 0 |
| odc +/+ wt | Jan. 17, 2011 | 4 | 4 | 0 | 0 | 0 |
| odc +/+ wt | Jan. 14, 2011 | 12 | 10 | 0 | 2 (19; 18) | 0 |
| odc +/− het | Jan. 14, 2011 | 7 | 4 | 0 | 3 (19, 19, 18) | 0 |
| odc +/+ wt | Jan. 13, 2011 | 5 | 3 | 0 | 2 (19, 19) | 0 |
| odc +/− het | Jan. 13, 2011 | 15 | 9 | 0 | 4 (19, 1×; 18, 3×) | 2 (19 + 0.5 × 2; 19 + 0.5 × 1) |
| odc +/+ wt | Dec. 3, 2010 | 6 | 4 | 0 | 2 (19, 19) | 0 |
| odc +/− het | Dec. 3, 2010 | 14 | 8 | 0 | 5 (19, 4×; 18) | 1 (17 + 0.5 × 2) |
| odc +/+ wt | Nov. 29, 2010 | 25 | 9 | 0 | 16 (19, 12×; 18, 4×) | 0 |
| odc +/+ wt | Nov. 26, 2010 | 23 | 15 | 0 | 8 (19, 5×; 18, 3×) | 0 |
| odc +/− het | Nov. 26, 2010 | 21 | 14 | 0 | 7 (19, 6×; 18) | 0 |
| odc +/− het | Nov. 25, 2010 | 10 | 9 | 0 | 1 (19) | 0 |
| odc +/+ wt | Nov. 25, 2010 | 46 | 28 | 0 | 17 (19, 12×; 18, 5×) | 1 (20 + 0.5 × 1) |

Table 5 Detailed breakdown of data shown in Table 4 (heterozygous odc mice)

| Treatment | N (cells) | Hypoploid 18 | Hypoploid 19 | Eupoloid 20 | Hyperploid 21 | Hyperploid 22 | PSSC | % Hyperploidy | % Aneuploidy |
|---|---|---|---|---|---|---|---|---|---|
| Control | 311 | 11 | 39 | 258 | 1 | 0 | 2 | 0.3 | 1.3 |
| DFMO | 261 | 12 | 41 | 191 | 3 | 0 | 14* | 1.1** | 7.7*** |

*P = 0.0006,
**P = 0.3358,
***P = 0.0002

Figure 5:
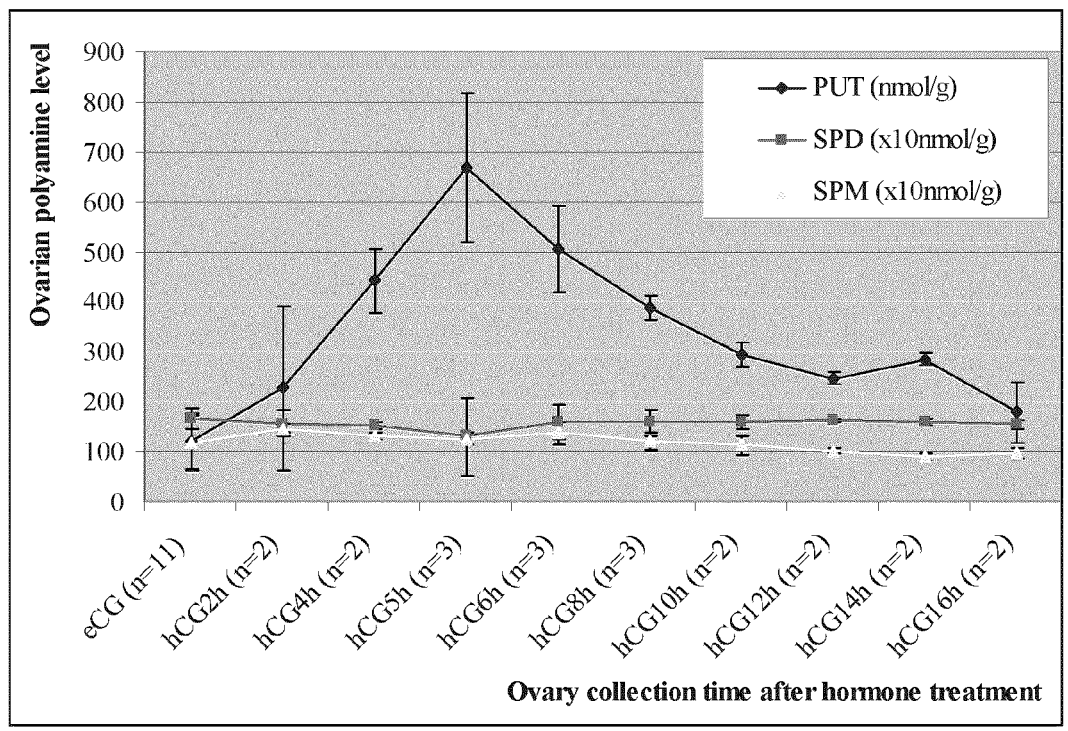
FIG. 5 is a graph that shows ovarian polyamine concentrations before (eCG) and at different times after hCG injection. Y-axis units are nmol/g for putrescine and ×10 nmol/g for spermine and spermidine.

Table 6 Young (7-8 weeks) CF1 mice were treated with regular drinking water (control) or 1% DFMO drinking water for 48 h (see FIG. 5 for details). Karyotype analyses were carried out by dual stains (anti-CREST and Sytox green) of metaphase II chromosomes. N: number of interpretable metaphase II karyotypes containing at least 18 dyads or the equivalent (e.g. 17 dyads plus 2 separated sister chromatids). Hypoploid: 18-19 dyads. Euploid: 20 dyads. Hyperploid: 21 or 22 dyads. PSSC: any karyotypes containing separated sister chromatid(s), with the total of at least 18 dyads or the equivalents. Aneuploid: 2×hyperploid+PSSC. Detailed breakdowns are in Table 7.

| Group | Date | N | Euploid | Hypoploid | Hyperploid | PSSC |
|---|---|---|---|---|---|---|
| DFMO | Jan. 27, 2010 | 43 | 26 | 15 (19, 10×; 18, 5×) | 0 | 2 (19 + 0.5 × 1; 18 + 0.5 × 2) |
| Control | Jan. 31, 2010 | 40 | 26 | 14 (19, 13×; 18) | 0 | 0 |
| DFMO | Feb. 1, 2010 | 55 | 35 | 19 (19, 15×; 18, 4×) | 1 (21) | 0 |

-continued

| Group | Date | N | Euploid | Hypoploid | Hyperploid | PSSC |
|---|---|---|---|---|---|---|
| Control | Mar. 22, 2010 | 18 | 13 | 5 (19, 4×; 18) | 0 | 0 |
| Control | May 1, 2010 | 24 | 23 | 1 (19) | 0 | 0 |
| DFMO | May 1, 2010 | 54 | 50 | 1 (19) | 0 | 3<br>20 + 0.5 × 1<br>20 + 0.5 × 1<br>19 + 0.5 × 1 |
| Control | May 7, 2010 | 18 | 17 | 1 (19) | 0 | 0 |
| DFMO | May 7, 2010 | 35 | 27 | 7 (19, 7×) | 1 (21) | 0 |
| Control | May 14, 2010 | 34 | 29 | 5 (19, 2×; 18, 3×) | 0 | 0 |
| DFMO | May 14, 2010 | 11 | 10 | 1 (18) | 0 | 0 |
| Control | May 23, 2010 | 27 | 24 | 3 (19; 19; 18) | 0 | 0 |
| DFMO | May 23, 2010 | 4 | 2 | 2 (19; 18) | 0 | 0 |
| Control | May 27, 2010 | 66 | 55 | 9 (19, 7×; 18, 2×) | 1 (21) | 1<br>19 + 0.5 × 1 |
| DFMO | May 27, 2010 | 36 | 26 | 5 (19, 5×) | 0 | 5<br>20 + 0.5 × 1<br>19 + 0.5 × 2<br>19 + 0.5 × 2<br>19 + 0.5 × 1<br>18 + 0.5 × 3 |
| Control | Jun. 7, 2010 | 49 | 45 | 3 (19; 19; 18) | 0 | 1<br>17 + 0.5 × 2 |
| DFMO | Jun. 7, 2010 | 23 | 15 | 3 (19; 19; 18) | 1 (21) | 4<br>20 + 0.5 × 1;<br>20 + 0.5 × 1;<br>19 + 0.5 × 1;<br>19 + 0.5 × 1 |
| Control | Jun. 11, 2010 | 35 | 26 | 9 (19, 7×; 18, 2×) | 0 | 0 |

Table 7 Detailed breakdown of data listed in Table 6 (DFMO in vivo). N: number of interpretable MII spreads with at least 18 dyads or the equivalents (e.g. 17+0.5×2 denotes 17 dyads plus two single sisters).

| | N | Hypoploid | Euploid | Hyperploid | | | | |
|---|---|---|---|---|---|---|---|---|
| Treatment | (cells) | 18 | 19 | 20 | 21 | 22 | PSSC | % Hyperploidy | % Aneuploidy |
| Control | 248 | 13 | 33 | 175 | 2 | 1 | 24 | 1.2 | 12.1 |
| DFMO | 80 | 5 | 9 | 50 | 2 | 0 | 14* | 2.5** | 22.5*** |

*P = 0.0702;
**P = 0.5989;
***P = 0.0287

Table 8 DFMO increases the egg aneuploidy rate of young hybrid F1 females. GV oocytes isolated from young (7-8 weeks) hybrid F1 females, via crossing C57BL/6 females and SPRET/Ei males, were incubated for 17 h in αMEM (control) or αMEM containing 5 mM DFMO. Karyotype analyses were carried out by dual stains (anti-CREST and Sytox green) of metaphase II chromosomes. N: number of interpretable metaphase II karyotypes containing at least 18 dyads or the equivalent (e.g. 17 dyads plus 2 separated sister chromatids). Hypoploid: 18-19 dyads. Euploid: 20 dyads. Hyperploid: 21 or 22 dyads. PSSC: any karyotypes containing separated sister chromatid(s), with the total of at least 18 dyads or the equivalents. Aneuploid: 2×hyperploid+PSSC. Detailed breakdowns are in Table 9.

| Group | Date dd/mm/yyyy | Countable | Euploid | Hypoploid | Hyperploid | PSSC |
|---|---|---|---|---|---|---|
| Control | 10 Jan. 2010 | 2 | 0 | 2 (19; 19) | 0 | 0 |
| DFMO | 12 Jan. 2010 | 7 | 3 | 1 (19) | 1 (21) | 2 (20 + 0.5 × 1; 19 + 0.5 × 2) |
| Control | 14 Jan. 2010 | 22 | 8 | 11 (19, 4×; 18, 7×) | 1 (21) | 2 (18 + 0.5 × 1; 18 + 0.5 × 1) |
| Control | 20 Jan. 2010 | 12 | 6 | 3 (19, 3×) | 1 (22) | 2 (20 + 0.5 × 2; 19 + 0.5 × 3) |
| DFMO | 20 Jan. 2010 | 5 | 2 | 2 (19; 18) | 1 (21) | 0 |
| Control | 23 Jan. 2010 | 4 | 1 | 3 (19; 19; 18) | 0 | 0 |
| DFMO | 23 Jan. 2010 | 1 | 0 | 1 (19) | 0 | 0 |
| Control | 10 Feb. 2010 | 1 | 1 | 0 | 0 | 0 |
| DFMO | 10 Feb. 2010 | 6 | 2 | 4 (19, 3×; 18) | 0 | 0 |
| Control | 9 Mar. 2010 | 12 | 11 | 0 | 0 | 1 (18 + 0.5 × 2) |
| Control | 20 Mar. 2010 | 4 | 3 | 1 (18) | 0 | 0 |
| Control | 3 Jun. 2010 | 26 | 18 | 6 (19, 6×) | 0 | 2 (19 + 0.5 × 1; 18 + 0.5 × 4) |
| DFMO | 3 Jun. 2010 | 11 | 8 | 1 (19) | 0 | 2 (19 + 0.5 × 2; 17 + 0.5 × 4) |
| Control | 29 Jun. 2010 | 3 | 2 | 1 (19) | 0 | 0 |
| DFMO | 29 Jun. 2010 | 5 | 5 | 0 | 0 | 0 |
| Control | 7 Jul. 2010 | 15 | 13 | 0 | 0 | 2 (18 + 0.5 × 3; 18 + 0.5 × 1) |
| DFMO | 7 Jul. 2010 | 5 | 3 | 0 | 0 | 2 (19 + 0.5 × 2; 19 + 0.5 × 2) |
| Control | 11 Jul. 2010 | 26 | 20 | 4 (19, 3×; 16) | 0 | 2 (20 + 0.5 × 1; 20 + 0.5 × 1) |
| DFMO | 11 Jul. 2010 | 25 | 17 | 4 (19; 18, 3×) | 0 | 4 (20 + 0.5 × 1; 19 + 0.5 × 2; 19 + 0.5 × 2; 19 + 0.5 × 1) |
| DFMO | 24 Jul. 2010 | 3 | 2 | 1 (19) | 0 | 0 |
| DFMO | 25 Jul. 2010 | 5 | 5 | 0 | 0 | 0 |
| Control | 27 Jul. 2010 | 5 | 5 | 0 | 0 | 0 |
| DFMO | 27 Jul. 2010 | 7 | 3 | 0 | 0 | 4 (20 + 0.5 × 1; 20 + 0.5 × 1; 19 + 0.5 × 2; 18 + 0.5 × 1) |
| Control | 30 Jul. 2010 | 12 | 12 | 0 | 0 | 0 |
| Control | 28 Oct. 2010 | 42 | 31 | 3 (19, 3×) | 0 | 8 (20 + 0.5 × 2; 20 + 0.5 × 1; 20 + 0.5 × 1; 20 + 0.5 × 1; 19 + 0.5 × 2; 19 + 0.5 × 1; 18 + 0.5 × 2; 17 + 0.5 × 2) |
| Control | 30 Oct. 2010 | 13 | 9 | 3 (19; 18; 18) | 1 (21) | 0 |
| Control | 5 Nov. 2010 | 49 | 34 | 10 (19, 8×; 18, 2×) | 0 | 5 (19 + 0.5 × 2; 19 + 0.5 × 1; 19 + 0.5 × 1; 19 + 0.5 × 1; 18 + 0.5 × 1) |

Table 9 Detailed breakdown of data listed in Table 8 (DFMO in F1 mice).

DFMO did not affect the number of MII eggs collected from the oviducts (control: 28.6/mouse, n=38 vs. DFMO: 29.3/mouse, n=37), indicating normal folliculogenesis and ovulation. However, DFMO caused a significant increase of aneuploidies in ovulated eggs, from 1.3% to 7.7%. Furthermore, a majority of the aneuploidies involved PSSC (Table 6 and Table 7).

To rule out any possibility that chromosome spreading procedures may artificially separate sister chromatids and complicate the DFMO results, 2-cell embryo karyotyping was carried out which does not rely on the presence of single sister chromatids to assess aneuploidy. Again, DFMO treatment significantly increased the occurrence of hyperploid 2-cell embryos, from 0 to 10.4% (Table 10, and Table 11).

| Treatment | N 2-cells | Euploid 40 | Hypoploid 39 | Hyperploid 41 |
|---|---|---|---|---|
| Control | 59 | 51 | 8 | 0 |
|  |  | 86.4% | 13.6% | 0% |
| DFMO | 48 | 38 | 5 | 5 |
|  |  | 79.2% | 10.4% | 10.4% |

* P = 0.0161

Table 10 DFMO in mouse drinking water increases hyperploid 2-cell embryos. Young (7-8 weeks) CF1 mice were treated with regular water (control), or 1% DFMO drinking water for 48 h, prior to mating (see FIG. 5 for details). Embryos (2-cell) were isolated and subjected to karyotype analyses. N: Total interpretable 2-cell embryos. Euploid: 40 chromosomes in each of the two blastomeres, or 40 chromosomes in one blastomere with the other blastomere having less than 40 chromosomes or uninterpretable/lost. Hypoploid: 39 chromosomes in each of the two blastomeres, or 39 in one blastomere with the other less than 39 or uninterpretable/lost. Hyperploid: 41 chromosomes in at least one blastomere (we found no 42 or more chromosomes in this study). Detailed breakdowns are in Table 11.

| Group | Date | Mice | 2-cell stage embryos# | N | Phenotype | |
|---|---|---|---|---|---|---|
| Control | May 6, 2011 | 1 | 4 | 2 | 40 + 38 1× | 40 1× |
| Control | May 18, 2011 | 3 | 5 | 5 | 40 + 40 5× | |
|  |  |  |  |  | 40 + 40 18× | 40 7× |
|  |  |  |  |  | 39 + 39 1× | 39 1× |
|  |  |  |  |  | 40 + 39 6× | |
| Control | May 19, 2011 | 3 | 78 | 42 | 40 + 38 5× | |
|  |  |  |  |  | 40 + 34 1× | |
|  |  |  |  |  | 39 + 38 2× | |
|  |  |  |  |  | 39 + 37 1× | |
|  |  |  |  |  | 40 + 40 2× | 40 4× |
| Control | May 20, 2011 | 3 | 18 | 10 | 40 + 39 1× | 39 1× |
|  |  |  |  |  | 39 + 37 1× | |
|  |  |  |  |  | 39 + 35 1× | |
| DFMO | May 27, 2011 | 5 | 12 | 5 | 40 + 39 1× | 41 1× |
|  |  |  |  |  | 40 + 38 2× | 40 1× |
|  |  |  |  |  | 40 + 41 1× | 40 4× |
| DFMO | May 28, 2011 | 6 | 14 | 13 | 40 + 40 6× | 39 1× |
|  |  |  |  |  | 40 + 38 1× | |
| DFMO | Jun. 6, 2011 | 10 | 12 | 5 | 40 + 40 2× | 40 1× |
|  |  |  |  |  | 40 + 39 2× | |
|  |  |  |  |  | 41 + 41 1× | 41 1× |
|  |  |  |  |  | 40 + 40 6× | 40 6× |
|  |  |  |  |  | 39 + 39 2× | 39 2× |

-continued

| Group | Date | Mice | 2-cell stage embryos# | N | Phenotype |
|---|---|---|---|---|---|
| DFMO | Jun. 8, 2011 | 10 | 81 | 25 | 41 + 40 1× |
|  |  |  |  |  | 40 + 39 1× |
|  |  |  |  |  | 40 + 38 2× |
|  |  |  |  |  | 40 + 37 1× |
|  |  |  |  |  | 40 + 35 1× |
|  |  |  |  |  | 40 + 34 1× |

Table 11 Detailed breakdown of data listed in Table 10 (2-cell embryo karyotypes). N: number of interpretable 2-cell embryos. Under "phenotype" in left column are those with two countable blastomeres (e.g. 40+38 or 40+40) followed by the numbers of such embryos (e.g. 1× or 5×). In the right column under "phenotype" are those with only one countable blastomere.

Two other mouse models were additionally used. First, DFMO was tested as a potential treatment to increase egg aneuploidy in the hybrid F1 females that has a high baseline aneuploidy rate similar to human (Koehler et al., 2006). The interspecies F1 females, from crossing female C57BL/6 (*Mus musculus*) and male SPRET/Ei mice (*Mus spretus*), exhibit impaired non-sister crossovers and therefore predispose oocytes to an increased risk of aneuploidy (Koehler et al., 2006).

The authors of the present disclosure have now shown that MII eggs derived from IVM of young F1 females exhibited a high aneuploidy rate (12.1%), comparable to that (10.1%) previously determined in ovulated eggs (Koehler et al., 2006). The presence of 5 mM DFMO in IVM medium indeed significantly increased egg aneuploidy rate to 22.5% (Table 8, and Table 9), indicating that reducing ODC activity in mice of a different genetic background also increases egg aneuploidy. Second, heterozygous odc mice (Pendeville et al., 2001) were examined for exhibition of elevated egg aneuploidy. Analyzing ovarian ODC activity indicated ~40% reduction in heterozygous odc mice, compared to age-matched wild-type littermates (FIG. 1). Analyzing oviduct-derived eggs indicated an elevation in egg aneuploidy in heterozygous odc mice, compared to age-matched wild-type litter-mates, although the difference has not reached statistical significance (Table 4, and Table 5).

EXAMPLE 3

Age-Dependent Reduction of Ovarian ODC Activity

The authors of the present disclosure have also found age-dependent reduction of ovarian ODC activity, reaching ~⅓ in 8-month-old C57BL/6 mice (FIG. 2, 3). To determine if indeed older mice exhibit diminished ODC expression in the oocytes, immunohistological analyses of ovarian sections was carried out according to Bastida et al. (Bastida et al., 2005). Using three different animals in each group, the authors of the present disclosure demonstrated that antral follicles in 8-month-old mice exhibited significantly reduced levels of hCG-induced ODC expression in both the oocyte and somatic cells (Tao and Liu, 2013).

EXAMPLE 4

Putrescine and ODC

It remains unknown how ODC/putrescine deficiency increases the risk of aneuploidy pregnancy. No evidence of spindle abnormality was found, either in ODC-deficient young oocytes or in oocytes of very old heterozygous odc mice (Table 12, Tao and Liu, 2013). However, the prevalence of PSSC in ODC-deficient young eggs (Table 6 and Table 8) suggested to the authors of the present disclosure that optimal putrescine concentration may have an important role in maintaining sister chromatid cohesion during meiosis I. This role may be indirect (e.g. via its suppression of oxidative stress, Zhou et al., 2009), given the low phenotypic penetrance, in both the number of aneuploid oocytes and the number of chromosomes in affected oocytes, even when the transitory ODC rise was completely inhibited (FIG. 2, 3). PSSC is also the dominant form of aneuploidies in eggs of older mice (Table 13), which exhibited significantly reduced level of ODC and putrescine. Therefore, aging-related partial loss of chromosome-associated cohesin predisposes these oocytes to increased risk of losing centromeric cohesion in meiosis I (Lister et al., 2010; Chiang et al., 2010). This increased risk, together with the diminished ODC activity (FIG. 2, 3), leads to increased incidence of PSSC. The authors of the present disclosure believe that restoration of optimal putrescine concentrations in the ovaries and the oocytes of older mice may protect at least some of the vulnerable entromeric cohesion during meiosis I (Table 13, with a detailed break-down show in Table 14).

| Group | Oocyte recovery | N | GV | MI | PB1 | frag-mented | dead | Normal MI spindle |
|---|---|---|---|---|---|---|---|---|
| Old - control | 62/12 mice | 32 | 7 | 23 | 1 | 0 | 1 | 22/23 |
| Old - Putrescine | | 30 | 6 | 21 | 2 | 0 | 1 | 19/20* |
| Young - control | 55/2 mice | 55 | 13 | 33 | 5 | 2 | 4 | 32/33 |

Table 12 Summary of two independent experiments. N: total numbers of oocytes in two experiments; GV: oocytes remained in prophase I; MI, no germinal vesicle and no polar body seen (used for spindle examination); PB1, oocytes with first polar body; Fragmented: abnormal cleavage likely due to parthenogenetic activation. * one MI oocyte was lost during handling.

| | N | Hypoploid | | Euploid | Hyperploid | | | | |
|---|---|---|---|---|---|---|---|---|---|
| Treatment | (cells) | 18 | 19 | 20 | 21 | 22 | PSSC | % Hyperploidy | % Aneuploidy |
| Control | 142 | 7 | 12 | 106 | 1 | 0 | 16 | 0.7 | 12.7 |
| Putrescine | 114 | 4 | 21 | 83 | 0 | 0 | 6 | 0 | 5.3* |

Table 13 Putrescine supplementation reduces egg aneuploidy in old mice. C57BL/6 (8 months) mice were treated with regular drinking water (control) or 1% putrescine drinking water for one week (resulting in a dose of about 1 g of putrescine/kg body weight per day). GV oocytes isolated from the ovaries of control mice were incubated for 17 h in αMEM. Oocytes isolated from putrescine treated mice were incubated for 17 h in αMEM containing 5 mM putrescine. Metaphase II eggs following IVM were karyotyped and data expressed. Karyotype analyses were carried out by dual stains (anti-CREST and Sytox green) of metaphase II chromosomes. N: number of interpretable metaphase II karyotypes containing at least 18 dyads or the equivalent (e.g. 17 dyads plus 2 separated sister chromatids). Hypoploid: 18-19 dyads. Euploid: 20 dyads. Hyperploid: 21. PSSC: any karyotypes containing separated sister chromatid(s), with the total of at least 18 dyads or the equivalents. Aneuploid: 2×hyperploid+PSSC. Detailed breakdowns are in Table 14.

| Group | Date | N | Euploid | Hypoploid | Hyperploid | PSSC |
|---|---|---|---|---|---|---|
| Putrescine | Feb. 23, 2011 | 58 | 38 | 16 (19, 13×; 18, 3×) | 0 | 4 19 + 0.5 × 2; 9 + 0.5 × 1; 19 + 0.5 × 1; 17 + 0.5 × 5 |
| Putrescine | Feb. 15, 2011 | 45 | 38 | 5 (19, 5×) | 0 | 2 20 + 0.5 × 1; 19 + 0.5 × 1 |
| Control | Feb. 15, 2011 | 54 | 44 | 6 (19, 4×; 18, 2×) | 0 | 4 19 + 0.5 × 1; 19 + 0.5 × 1; 18 + 0.5 × 2; 17 + 0.5 × 3 |
| Putrescine | Feb. 9, 2011 | 11 | 7 | 4 (19, 3×; 18, 1×) | 0 | 0 |

-continued

| Group | Date | N | Euploid | Hypoploid | Hyperploid | PSSC |
|---|---|---|---|---|---|---|
| Control | Feb. 9, 2011 | 45 | 34 | 6 (19, 5×; 18, 1×) | 0 | 5; 20 + 0.5 × 1; 20 + 0.5 × 1; 19 + 0.5 × 2; 19 + 0.5 × 2; 19 + 0.5 × 1 |
| Control | Jan. 15, 2011 | 12 | 9 | 2 (19, 18) | 0 | 1; 17 + 0.5 × 2 |
| Control | Jan. 14, 2011 | 9 | 6 | 2 (19, 18) | 0 | 1; 18 + 0.5 × 2 |
| Control | Aug. 14, 2011 | 0 | 0 | 0 | 0 | 0 |
| Control | Aug. 12, 2010 | 2 | 1 | 0 | 0 | 1; 20 + 0.5 × 1 |
| Control | Aug. 11, 2010 | 5 | 3 | 1 (18) | 0 | 1; 18 + 0.5 × 2 |
| Control | Aug. 5, 2010 | 10 | 7 | 0 | 1 (21) | 2; 17 + 0.5 × 2; 16 + 0.5 × 2 |
| Control | Jul. 30, 2010 | 5 | 2 | 2 (19, 18) | 0 | 1; 19 + 0.5 × 2 |

Table 14 Detailed breakdown of data listed in Table 13 (putrescine in old mice)

The finding of PSSC as the dominant form of aneuploidies in ODC-deficient mice (young and old, see Table 3) is in contrast to the recent studies that suggest whole chromosome nondisjunction as the main form of aneuploidies in aged mice (Selesniemi et al., 2011; Merriman et al., 2012). While Selesniemi et al. employed DAPI staining of chromosomes in karyotyping (Selesniemi et al., 2011), Merriman et al. (Merriman et al., 2012) employed a novel in situ karyotyping method based on fluorescence confocal imaging of monastral-treated oocytes (Duncan et al., 2009). This method, which stains both chromosomes and centromeres (CREST) in fixed oocytes, has the distinct advantage of preserving all chromosomes (Duncan et al., 2009; Merriman et al., 2012). However, its identification of PSSC based on odd number of CREST dots (Merriman et al., 2012) likely underestimates the incidence of PSSC, as karyotypes that contain two separated sister chromatids are common forms of aneuploidies (Table 3).

The authors of the present disclosure employed the method developed by Hodges and Hunt (Hodges & Hunt, 2002) that involves the prior removal of zona pellucida so that the eggs are gently lysed in a hypotonic buffer (instead of the methanol:acidic acid fixative in the classical Takowski protocol (Evans, 1987)) during chromosome spreading. As a result, chromosomes remain closely and evenly positioned, often in a circular array, suggesting that all chromosomes "touch down" on the glass slide while still being associated with the spindle. This method also has the distinct advantage of preserving chromosome-associated proteins including CREST antigens (Hodges & Hunt, 2002), allowing simultaneous visualization of chromosomes and centromeres and hence unambiguous identification of PSSC. In all PSSC spreads, very few, mostly just one or two, separated sisters were present together with perfectly preserved chromosome dyads (Table 3), arguing against any possibility that the sisters are separated as a result of procedural artifact. Furthermore, in those PSSC karyotypes with two (or more) separated sisters, the sisters were randomly positioned in the chromosome array with no association with one another at all, suggesting that they exist as single sisters in the metaphase II spindle before spreading. Interestingly, in most, if not all, of the oocytes (Table 3) involving two separated sisters, the sisters appeared to belong to the same chromosome (Tao and Liu, 2013). Therefore, the affected sisters were segregated correctly during oocyte maturation (anaphase I) but became separated before the assembly of the metaphase II spindle in the mature egg. Such segregation errors appear to be the major form of aneuploidies in old oocytes, as supported by live cell imaging studies (Chiang et al., 2010). Finally, an independent method, karyotyping 2-cell embryos, which does not rely on the assessment of separated sisters, was employed to confirm the key finding that ODC deficiency causes increased aneuploidies (Table 10). The absence of hyperploid 2-cell embryos (0/59) in the control group indicates the extremely low incidence of aneuploidies in sperm and in first embryo mitosis, thus validating this as an alternative method of karyotyping the eggs.

EXAMPLE 5

Putrescine Administration Reduces Egg Aneuploidies in Older Mice

To determine if the diminished ovarian ODC activity contributes to egg aneuploidies in older mice, rescue experiments using putrescine supplementation were also carried out. Preliminary experiments indicated that injecting old C57BL/6 mice (8 months) with eCG followed by hCG failed to produce consistent ovulation. Therefore, IVM experiments were carried out which revealed that oocytes from these mice exhibited high aneuploidy rate (12.7%). For the rescue experiments, 1% putrescine was added to all drinking water for 7 days, refreshed daily, followed by IVM in the presence of 5 mM putrescine. This combination reduced egg aneuploidies to 5.3%. Putrescine supplementation in mouse drinking water did not change the number of fully grown GV oocytes in the ovaries (control: 26.4/mouse, n=12 vs. 25.3/mouse, n=13; these numbers are similar to the 27.5 produced by 8-week old C57BL/6 mice) (Table 13, Tao and Liu, 2013). Analyses of very old (16 months) odc−/+ mice, with or without putrescine supplementation, revealed no evidence of spindle abnormality or premature polar body emission (Table 12, Tao and Liu, 2013).

In summary, older mice (8 months of age) exhibited about ⅓ that of young mice in LH-stimulated ovarian ODC activity and exhibited a corresponding increase of egg aneuploidies. A combination of putrescine supplementation in mouse drinking water leading up to oocyte retrieval and in oocyte maturation medium reduced egg aneuploidies (number of aneuploid eggs/total number of eggs) of the old mice from 12.7% to 5.3%.

EXAMPLE 6

Peri-Ovulatory Putrescine Supplementation Reduced Mid-Gestation Embryo Deaths in Older Mice Live aneuploid births appear exceedingly infrequently in mice, young or old, with Goodlin, R. C. (Goodlin, R. C. 1965) finding no aneuploids in analyzing a total of 750 live births to 1.5 year old F1 females from BALBcx129 crosses. This rate may not be different from the estimated overall rate of 0.3% for aneuploidies among all human live births (Hassold, T. and Hunt, P 2001).

Since old mice exhibit a significant egg aneuploidy rate (Pan, H. et al. 2008, and Merriman, J. A. et al 2012) it follows that a majority of aneuploid embryos die during gestation, as is the case in humans (Baird, D. T. et al. 2005, and Chard, T. 1991). Indeed, old mice exhibit a significantly increased rate of embryo deaths (resorption), when 9-10 month old Theiler's original (TO) mice were examined at E15. Therefore, embryo resorption may be used as an indirect indicator of egg aneuploidy.

As discussed herein, old mice which are ODC deficient exhibited an increase in embryo resorption rate. This resorption rate increase may be reversed by feeding mice drinking water supplemented with 1% putrescine, the direct product of ODC enzymatic activity. While mice about 9-months of age exhibited significantly elevated levels of embryo resorption rate, putrescine supplementation 5-8 days up to the appearance of a vaginal plug (indicative of mating) reduced the embryo resorption rate to levels comparable to those in mice at about 8-weeks of age, as evidenced by the results illustrated in Table 15, which is a summary of the mating experiments with 9-month-old CF1 mice (control vs. putrescine), as well as 8-week-old mice. Putrescine treatment reduced the number of dead embryos observed on E12, from 1.6 to 0.8 per pregnancy. This reduction was also obvious when the ratio of dead embryos over total implantation sites were compared (12.5% vs. 6% for the putrescine and control groups, respectively). Similar analyses of 10 young mice yielded a ratio of 3.6% (dead embryos/total implantation sites on E12). Furthermore, peri-ovulatory putrescine supplementation was found to be safe for gestation, as judged by the perfectly normal embryos found on E12 (Table 15) and normal full term births. This is in contrast to a previous study which reported toxicity if excess putrescine was present during gestation (Pendeville, H. et al. 2001). In fact, the authors of the present disclosure treated young CF1 mice with as much as 10 mM putrescine in drinking water for the entire gestation period and found no signs of toxicity, to mother or fetuses, even though Penderville H. et al, stated that fetal toxicity was found at 1 mM putrescine in drinking water.

These results suggest that peri-ovulatory putrescine supplementation is effective in reducing embryo resorption, which is equivalent to miscarriages in humans. Furthermore, these results also indicate that peri-ovulatory putrescine supplementation is safe for gestation.

EXAMPLE 7

Putrescine Exhibit Transient Rise in the Ovaries During Ovulation

During estrous cycle in rats (Kobayashi 1971) and mice (Bastida et al. 2005), ovarian ODC activity exhibits a luteinizing hormone(LH)-mediated transitory rise during the evening of proestrus, concurrent with oocyte maturation in vivo. Within the ovaries, LH stimulates the transitory rise of ODC mainly in antral follicles (Icekson et al. 1974), both in the somatic (theca and granulosa) cells and in the oocytes (Bastida et al. 2005) (Tao and Liu 2013). Curiously, complete inhibition of this transient ODC/putrescine rise does not affect oocyte maturation or ovulation (Bastida et al. 2005, and Fozard 1980). It has been suggested that the transitory rise of ovarian ODC activity is required for luteinization of the granulosa cells to produce progesterone (Bastida et al. 2005), although gestation appears normal when the transient ODC/putrescine rise is inhibited (Fozard 1980).

A Dionex ion chromatography system was used to analyze polyamines during ovulation. This system employs an online conductivity detector coupled with an anion suppressor such that only cations are detected. Ovaries were extracted in 5% trichloric acid (TCA) followed by extraction with diethyl ether. The TCA extracts were diluted in water before being applied to the ion chromatography system. Prior to hCG injection, ovaries contained barely detectable levels of putrescine, compared to high concentrations of spermidine and spermine. Following hCG injection, ovaries exhibited a significant increase of putrescine, while spermidine and spermine levels remained unchanged.

Figure 6:
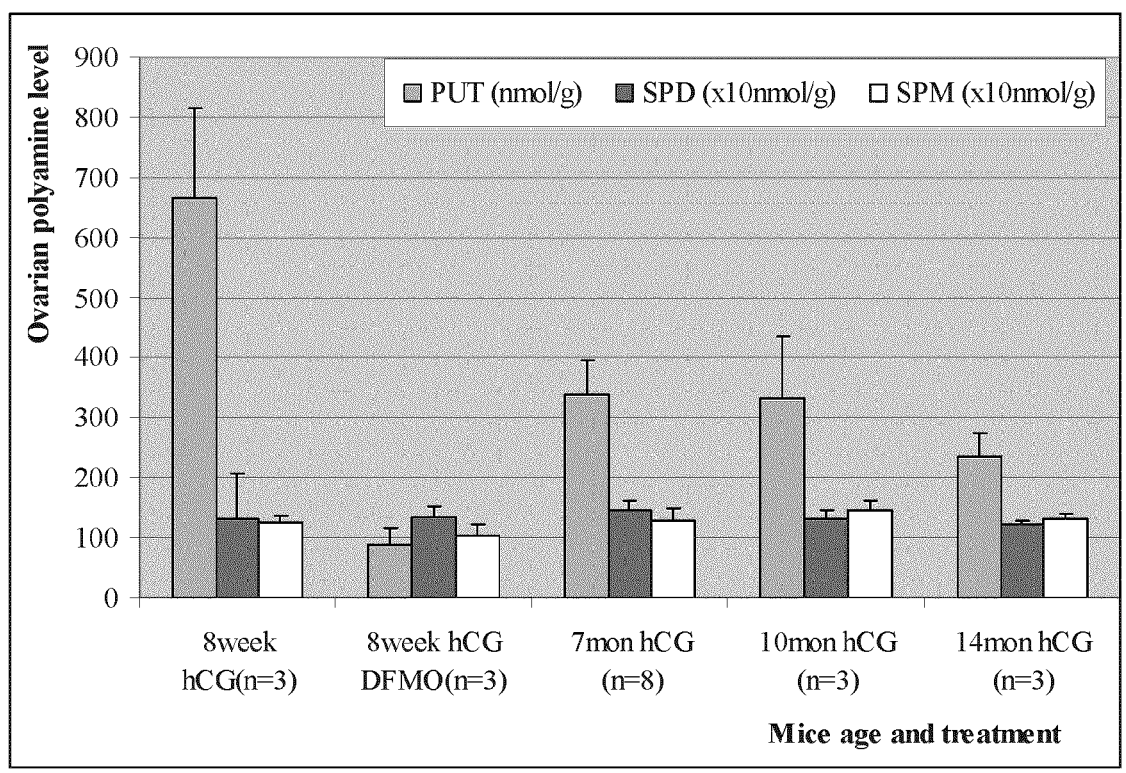
FIG. 6 is a graph that shows ovarian polyamine levels in mice of different ages at 5 hrs after hCG injection. Y-axis units are nmol/g for putrescine and ×10 nmol/g for spermine and spermidine.

Time course experiments indicated that the ovaries exhibited hCG-induced increase of putrescine, peaking at 5 h after hCG injection with 667 nmol per g of ovarian tissues, compared to 118 nmol per g prior to hCG injection (FIG. 5). This time course corresponded precisely to that of the transient ovarian ODC activity increase (Bastida et al. 2005, and Tao and Liu 2013). Treating mice for 48 hours with 1% DFMO in drinking water leading up to the time of sacrifice completely eliminated the hCG-mediated putrescine increase (FIG. 6).

TABLE 15

| Old CF1 mice | Control | Putrescine | Young |
| --- | --- | --- | --- |
| Number | 31 | 29 | 10 |
| Plug observed | 25 | 25 | 9 |
| Total pregnancy | 20 | 24 | 6 |
| Plug pregnancy | 19/25 (76.00%) | 23/25 (92.00%) | 6/9 (66.67%) |
| Unplug pregnancy | 1/6 (16.67%) | 1/4 (25.00%) | 0/1 (0.00%) |
| Total implants | 257 | 300 | 84 |
| Total normal fetuses | 225 | 282 | 81 |
| Total normal fetuses/total animals | 225/31 (7.26) | 282/29 (9.27) | 81/10 (8.10) |
| Total normal fetuses/total pregnancies | 225/20 (11.25) | 282/24 (11.75) | 81/6 (13.50) |
| Total resorption sites | 32 | 18 | 3 |
| Total resorption sites/total animals | 32/31 (1.03) | 18/29 (0.62) | 3/10 (0.30) |
| Total resorption sites/total pregnancies | 32/20 (1.60) | 18/24 (0.75) | 3/6 (0.50) |
| Total resorption sites/total implants | 32/257 (12.45%)*** | 18/300 (6.00%)* | 3/84 (3.57%)** |

*P = 0.0109 between control and putrescine;
**P = 0.5871 between old putrescine and young control;
***P = 0.0214 between young and old Controls These data are consistent with previous demonstration that such DFMO treatment effectively inhibited ovarian ODC activity (Tao and Liu 2013). Clearly, mouse ovaries contain high steady state of spermidine and spermine, but exhibit highly dynamic putrescine levels during ovulation.

EXAMPLE 8

Age-Dependant Drop in Ovulation-Induced Ovarian Putrescine Levels are Improved by Peri-Ovulation Supplementation of Putrescine Ovarian putrescine levels exhibit a clear age-dependent drop, measuring about 50% in 7-10 month old CF1 mice and ~30% in 14-month old CF1 mice (FIG. 6). In contrast, there were no significant changes in the levels of ovarian spermidine or spermine (FIG. 6).

Figure 7:
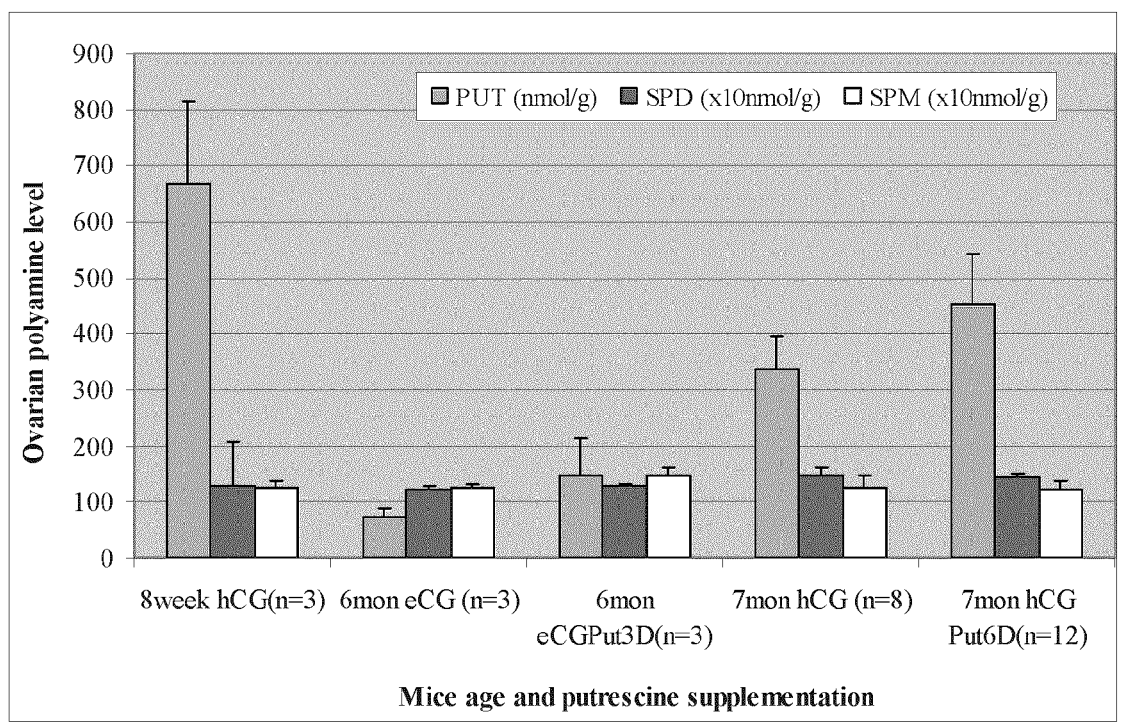
FIG. 7 is a graph that shows ovarian polyamine levels with or without putrescine supplementation for 3 days (Put3D) or 6 days (Put6D). The 3-day mice were treated with eCG alone and the 6-day mice were treated with both eCG followed by hCG. Y-axis units are nmol/g for putrescine and ×10 nmol/g for spermine and spermidine.

In an attempt to restore ovarian putrescine level in older mice to that found in young mice, mice were treated with oral putrescine supplementation (1% in drinking water) for several days up to the time of sacrifice. Analyzing ovarian extracts from these putrescine-treated mice indicated appreciably higher levels of ovarian putrescine either before or (5 h) after hCG injection, compared to control mice (FIG. 7). Levels of spermidine and spermine remained unchanged. It is worth noting that the ovarian putrescine level in the putrescine group after hCG was still less than that found in young mice (FIG. 7).

EXAMPLE 9

Pharmacokinetics of Putrescine Supplementation

Figure 8:
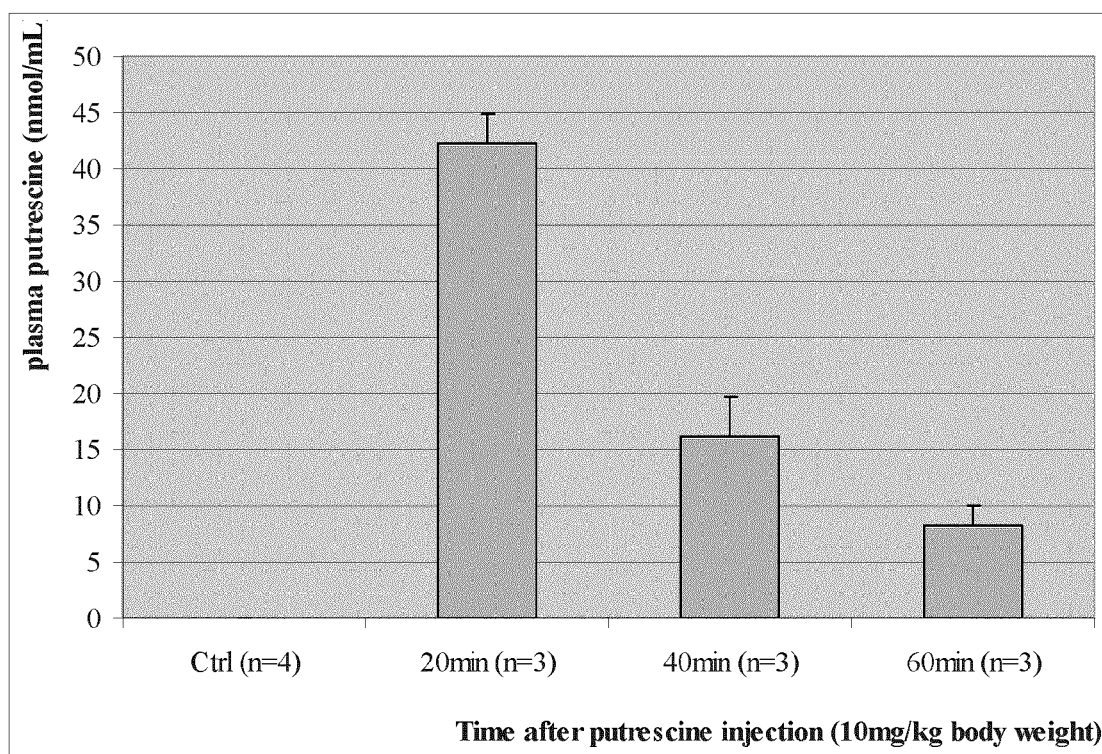
FIG. 8 is a graph that shows plasma putrescine levels in young mice at different times after a bolus injection of putrescine.

Exogenous putrescine was given to young mice. Plasma putrescine concentrations were determined. As shown in FIG. 8, prior to putrescine injection, the plasma putrescine was undetectable. Twenty (20) minutes after subcutaneous injection, plasma putrescine levels reached 42 nmol/mL. Thereafter, plasma putrescine levels rapidly decreased, measuring 16 nmol/mL and 8 nmol/mL, respectively, at 40 min and 60 min after putrescine injection.

ODC Deficiency and Human Pregnancy

Earlier studies by Angell and colleagues of surplus human IVF eggs have concluded that PSSC is the dominant form of aneuploidies and whole chromosome nondisjunction is rare (Angell, 1997; Angell, 1991; Angell et al., 1994). Others have reported both PSSC and whole chromosome nondisjunction in human eggs (Mahmood et al., 2000; Dailey et al., 1996). In contrast to these earlier studies, which involved relatively small number of human eggs, Kuliev et al. analyzed more than 20,000 human eggs (via their polar bodies) and concluded that, among the overall 31.1% aneuploidies, 93.7% are of PSSC phenotypes and only 6.3% are whole chromosome nondisjunction (Kuliev et al., 2011). This large study provides compelling support for the Angell hypothesis that PSSC is the dominant form of human egg aneuploidies (Wolstenholme & Angell, 2000); it also reiterates the extraordinarily high incidence of human egg aneuploidies, 31.1% with only 5 of the 23 chromosomes analyzed (Kuliev et al., 2011). It is estimated that only 30% of human conceptions result in live births. Another 10% are spontaneously aborted. The majority, 60%, are thought to be lost prior to clinical recognition of pregnancy (Baird et al., 2005). Egg aneuploidy, with dramatically increased incidences in older women, likely plays a dominant role in these "missing" human embryos, in miscarriages, and in birth defects (Hassold & Hunt, 2001).

In view of the above, and in view of the results of the mice studies discussed herein, the authors of the present disclosure believe that ovarian ODC deficiency may be an a factor in aneuploidies (such as maternal aging-related aneuploidies) in other mammals, such as humans. Accordingly, the authors of the present disclosure believe that administration of putrescine to women with reduced ovarian ODC activity level may reduce the rate of aneuploid conceptions, for example in a similar manner as putrescine supplementation reduced the aneuploid conception rate in mice.

Since putrescine is a naturally occurring metabolite and can easily and quickly enter the circulation system, the authors of the present disclosure believe that the women may be administered putrescine at least on the day of ovulation. In some examples, the women may be administered putrescine for one week up to and including the day of ovulation. In other examples, the women may be administered putrescine for one week up to the morning of egg retrieval for IVF patients. In yet another example, the women may be administered putrescine for 5-8 days up to and including the day of conception.

Some dosages and/or formulations of putrescine may reduce the aneuploidy rate for women with reduced ovarian ODC activity levels to an aneuploidy rate comparable to women with normal ovarian ODC activity levels. The women with reduced ovarian ODC activity levels may be, for example, women over 32 years of age. The women with normal ovarian ODC activity levels may be, for example, women between the ages of 18 and 25.

Experimental

Animals

CF1 mice and C57BL/6 mice were from Charles River (St-Constant, Quebec, Canada). SPRET/Ei mice (*Mus spretus*) were from Jackson lab (Bar Harbor, Me., US). F1 hybrids were generated by crossing C57BL/6 females to SPRET/Ei males. Heterozygous odc mice were produced in house and genotyping carried out according to Pendeville et al. (Pendeville et al., 2001). The animals were provided with water (or with the indicated drugs) and mouse chow ad libitum and housed in rooms illuminated for 12 h/day.

Oocyte Isolation and in Vitro Culture

Mice were euthanized by cervical dislocation 44-46 h after they were primed with 5 IU equine chorionic gonadotropin (eCG) intraperitonally. For putrescine supplementation, 1% putrescine was in all drinking water for 7 days until euthanization for experiments described in Table 13. Ovaries were immediately removed and minced in M2 medium (Sigma; unless otherwise indicated, other chemicals used in this study were also purchased from Sigma) to release oocytes. Oocytes with a clear germinal vesicle (GV) were used for in vitro maturation (IVM) for 17 hours in IVM medium (αMEM medium supplemented with 5% fetal bovine serum and 1 mM L-glutamine) overlaid with mineral oil.

In order to collect mature (metaphase II) oocytes in vivo (ovulation experiments) each mouse was injected with 5 IU human chorionic gonadotropin (hCG) intraperitoneally 44-46 h after eCG priming. The animals were euthanized 16-18 h after hCG injection and MII eggs were flushed out of oviducts in M2 medium and subjected to karyotype analyses as described below. For mice that were treated with 1% DFMO in drinking water, the drugs were present until the time of euthanization (see FIG. 4 for details).

To produce 2-cell embryos, mice were sequentially injected with eCG and hCG, as above for ovulation. After hCG injection, the females were caged singly with fertile young males overnight. For mice that were treated with 1% DFMO, the drug was withdrawn, and normal water resumed, at the time of hCG injection (see FIG. 4 for details). The females were separated from the males in the next morning (day 1 post coital or p.c.). Females were euthanized in the late morning on day 2 p.c., and the embryos were collected by flushing the oviducts with M2 medium. After three rinses in KSOM medium, the embryos were cultured 17 h in KSOM containing 0.02 μg/ml colchicine to cause metaphase arrest of the 2-cell embryos.

Oocyte and Embryo Chromosome Spread

Chromosome spread was carried out according to Hodges and Hunt (Hodges & Hunt, 2002) with minor modifications. In brief, oocytes or 2-cell embryos were collected in M2 medium. The zona pellucida was removed by treatment with 0.5 units/μl pronase at 37° C. for 20 sec. Zona-free oocytes/embryos were rinsed in M2 medium to detach polar bodies. The oocytes/embryos were individually plated onto glass slides (1-10 oocytes/embryos per slide) predipped in the fixative (prepared weekly and stored at 4° C.) containing 1% paraformaldehyde (w/v), 0.15% Triton X-100 (v/v), and 3 mM dithiothreitol, pH 9.2. Slides were kept overnight in moist boxes at room temperature. The slides were then rinsed in 0.5% Kodak Flo (Eastman Kodak Company, Rochester, N.Y.) solution and air-dried. The slides were incubated in 1:200 diluted human anti-centromere serum (Immunovision, Springdale, Ark.) in PBS containing 1% BSA overnight at 4° C., in 1:300 diluted secondary antibody (goat anti-human) conjugated with rhodamine (Jackson ImmunoResearch) in PBS-BSA for 1 h at room temperature, and 0.1% SYTOX green (Invitrogen, Eugene, Oreg.) in PBS for 30 min at room temperature. To avoid bias, the slides were coded by a colleague before being examined by an investigator using epifluorescence microscopy and photographed. Decoding was done after karyotypes were tabulated.

ODC Activity Assay

After 44-46 h eCG priming, or 6 h following the subsequent hCG injection, the ovaries were collected into Eppendorf tubes and frozen at −80° C. immediately till use. The ovaries were weighed and minced with optical scissors. Lysis buffer (25 mM Tris/HCl pH 7.2, 2 mM dithiothreitol, 0.1 mM EDTA, 0.25 M sucrose, 0.1% Triton X-100 (v/v); modified from Bastida et al. (Bastida et al., 2005) was added 25 μL per mg ovarian tissues and the resulting suspension homogenized by sonication (Fisher Sonic Demembrator, New York, USA) for 20 seconds thrice. The ovarian homogenates were centrifuged at 16,000×g for 10 min. Supernatants were applied to ODC assays (Zhou et al., 2009) in microtiter plates, each well containing 50 μL of lysate, plus 0.1 mM pyridoxyl-5-phosphate and 0.5 μCi (57.1 mCi/mmol) of 14C-labeled ornithine (PerkinElmer, Boston, Mass.). The wells were tightly covered with 3MM paper pre-wet in freshly prepared water-saturated $Ba(OH)_2$. The wells were incubated 1 h at 37° C. $^{14}CO_2$ released from decarboxylation reaction formed $Ba^{14}CO_3$ precipitates on filter. The 3MM paper was exposed to a Storage phosphor screen overnight to capture the latent images produced by 14C-emitted β radiation. The Storage phosphor screen was then scanned on Typhoon™ imaging system (GE Healthcare Life Sciences), resulting in digital images that were then quantified by Image Quant5.2 (GE Healthcare Life Sciences). ODC activity is expressed as relative light intensity in arbitrary units. To determine the absolute ODC activity in ovarian extracts (FIG. 2), the reaction strips with captured $Ba^{14}CO_3$ were exposed to the Storage phosphor screen alongside a strip spotted with a dilution series of known quantities of 14C-labeled ornithine, used for calibration.

Oral Supplementation of Putrescine in Mice 9-month-old female mice were supplemented with 1% putrescine in drinking water, or control drinking water. For the mice supplemented with putrescine, assuming that a 50-g lab mouse drinks 5 g of water per day, this would result in a dose of about 1 g of putrescine/kg of body weight.

Four (4) days later, the female mice are caged individually with fertile males (1:1) overnight. The females were examined in the morning for the presence of a vaginal plug (indicative of mating) and "plugged" females are considered E0 and separated from the males. Mice without a plug were continued mating until a plug was seen, or for up to a total of 4 days (average length of a mouse estrus cycle). Mice were sacrificed on E12 ("unplugged" mice were also sacrificed, taking the next morning following the 4-day-mating as E0) and their uterine horns inspected for normal embryos and dead embryos (resorption). As a control, similar experiments were conducted with young mice (8 weeks).

Ovarian Polyamine Quantification

Polyamines from ovarian samples were determined by ion chromatography (IC) system (Rey and Pohl, 2003. J. Chromatography A 997:199-206). Ovaries were collected immediately after animal sacrifice and stored at −80° C. until use. The samples were thawed and minced, and then 5% trichloroacetic acid (TCA) was added (20 μl/mg). The samples were ultra-sonicated 30 seconds thrice. After centrifugation, the supernatants were extracted twice with diethyl ether. The mouse blood was collected in a tube containing 1 iu/ml heparin (LEO). After centrifugation, the supernatant (plasma) was collected and 10% TCA was added by 1:1 in volume. These plasma samples were extracted twice with diethyl ether, as noted above. The extracts were diluted 10 times in water for polyamine analysis on Dionex Ion ICS-2100 system (Thermo scientific, Dionex, Sunnyvale, Calif., USA) according to the manufacture instructions, using the support software of PeakNet 6.40 SP5 Build 778. To quantify the polyamine concentrations, a standard curve was established with serial dilutions of putrescine, spermidine and spermine.

Statistics

All statistical analyses were performed using GraphPad Prism 5.02. The data in chromosomal spread were analyzed by Fisher's Exact test (two-tailed). The P values are indicated in the tables.

In the preceding description, for purposes of explanation, numerous details are set forth in order to provide a thorough understanding of the examples. However, it will be apparent to one skilled in the art that these specific details are not required.

The above-described examples are intended to be exemplary only. Alterations, modifications and variations can be effected to the particular examples by those of skill in the art without departing from the scope, which is defined solely by the claims appended hereto.

REFERENCE LIST

Angell R (1997). First-meiotic-division nondisjunction in human oocytes. Am. J. Hum. Genet. 61, 23-32.

Angell R R (1991). Predivision in human oocytes at meiosis I: a mechanism for trisomy formation in man. Hum. Genet. 86, 383-387.

Angell R R, Xian J, Keith J, Ledger W, Baird D T (1994). First meiotic division abnormalities in human oocytes: mechanism of trisomy formation. Cytogenet. Cell Genet. 65, 194-202.

Baird D T, Collins J, Egozcue J, Evers L H, Gianaroli L, Leridon H, Sunde A, Templeton A, Van S A, Cohen J, Crosignani P G, Devroey P, Diedrich K, Fauser B C, Fraser L, Glasier A, Liebaers I, Mautone G, Penney G, Tarlatzis B (2005). Fertility and ageing. Hum. Reprod. Update. 11, 261-276.

Bastida C M, Cremades A, Castells M T, Lopez-Contreras A J, Lopez-Garcia C, Tejada F, Penafiel R (2005). Influence of ovarian ornithine decarboxylase in folliculogenesis and luteinization. Endocrinology 146, 666-674.

Chard, T (1991) Frequency of implantation and early pregnancy loss in natural cycles. Baillieres Clin. Obstet. Gynaecol. 5, 179-189.

Chiang T, Duncan F E, Schindler K, Schultz R M, Lampson M A (2010). Evidence that weakened centromere cohesion is a leading cause of age-related aneuploidy in oocytes. Curr. Biol. 20, 1522-1528.

Dailey T, Dale B, Cohen J, Munne S (1996). Association between nondisjunction and maternal age in meiosis-II human oocytes. Am. J. Hum. Genet. 59, 176-184.

Duncan F E, Chiang T, Schultz R M, Lampson M A (2009). Evidence that a defective spindle assembly checkpoint is not the primary cause of maternal age-associated aneuploidy in mouse eggs. Biol. Reprod. 81, 768-776.

Evans, E. P. (1987). Karyotying and sexing of gametes, embryos and fetuses and in situ hybridization to chromosomes. In Mammalian Development: a practical approachl, M. Monk, ed. (Washington D.C.: IRL Press), p. 263.

Fozard J R, Part M L, Prakash N J, Grove J, Schechter P J, Sjoerdsma A, Koch-Weser J (1980a). L-Ornithine decarboxylase: an essential role in early mammalian embryogenesis. Science 208, 505-508.

Fozard J R, Prakash N J, Grove J (1980b). Ovarian function in the rat following irreversible inhibition of L-ornithine decarboxylase. Life Sci. 27, 2277-2283.

Garcia-Faroldi G, Correa-Fiz F, Abrighach H, Berdasco M, Fraga M F, Esteller M, Urdiales J L, Sanchez-Jimenez F, Fajardo I (2009). Polyamines affect histamine synthesis during early stages of IL-3-induced bone marrow cell differentiation. J. Cell Biochem. 108, 261-271.

Goudlin R C (1965). Non-disjunction and maternal age in the mouse. J. Reprod. Fertil. 9, 355-356.

Hassold T, Hunt P (2001). To err (meiotically) is human: the genesis of human aneuploidy. Nat. Rev. Genet. 2, 280-291.

Hodges C A, Hunt P A (2002). Simultaneous analysis of chromosomes and chromosome-associated proteins in mammalian oocytes and embryos. Chromosoma 111, 165-169.

Icekson I, Kaye A M, Lieberman M E, Lamprecht S A, Lahav M, Lindner H R (1974). Stimulation by luteinizing hormone of ornithine decarboxylase in rat ovary: preferential response by follicular tissue. J. Endocrinol. 63, 417-418.

Kobayashi Y, Kupelian J, Maudsley D V (1971). Ornithine decarboxylase stimulation in rat ovary by luteinizing hormone. Science 172, 379-380.

Koehler K E, Schrump S E, Cherry J P, Hassold T J, Hunt P A (2006). Near-human aneuploidy levels in female mice with homeologous chromosomes. Curr. Biol. 16, R579-R580.

Kuliev A, Zlatopolsky Z, Kirillova I, Spivakova J, Cieslak J J (2011). Meiosis errors in over 20,000 oocytes studied in the practice of preimplantation aneuploidy testing. Reprod. Biomed. Online. 22, 2-8.

Lefevre P L, Palin M F, Murphy B D (2011). Polyamines on the reproductive landscape. Endocr. Rev. 32, 694-712.

Lister L M, Kouznetsova A, Hyslop L A, Kalleas D, Pace S L, Barel J C, Nathan A, Floros V, Adelfalk C, Watanabe Y, Jessberger R, Kirkwood T B, Hoog C, Herbert M (2010). Age-related meiotic segregation errors in Mammalian oocytes are preceded by depletion of cohesin and Sgo2. Curr. Biol. 20, 1511-1521.

Mahmood R, Brierley C H, Faed M J, Mills J A, Delhanty J D (2000). Mechanisms of maternal aneuploidy: FISH analysis of oocytes and polar bodies in patients undergoing assisted conception. Hum. Genet. 106, 620-626.

Merriman J A, Jennings P C, McLaughlin E A, Jones K T (2012). Effect of aging on superovulation efficiency, aneuploidy rates, and sister chromatid cohesion in mice aged up to 15 months. Biol. Reprod. 86, 49.

Metcalf B W, Bey P, Danzin C, Jung M J, Casara P, Vevert J P (1978). Catalytic irreversible inhibition of mammalian ornithine decarboxylase (E.C.4.1.1.17) by substrate and product analogues. J. Am. Chem. Soc. 100, 2551-2553.

Nilsson J A, Keller U B, Baudino T A, Yang C, Norton S, Old J A, Nilsson L M, Neale G, Kramer D L, Porter C W, Cleveland J L (2005). Targeting ornithine decarboxylase in Myc-induced lymphomagenesis prevents tumor formation. Cancer Cell 7, 433-444.

Pan, H, Ma, P, Zhu, W, Schultz, R M (2008). Age-associated increase in aneuploidy and changes in gene expression in mouse eggs. Dev. Biol. 316, 397-407.

Pegg A E (2006). Regulation of ornithine decarboxylase. J. Biol. Chem. 281, 14529-14532.

Pendeville H, Carpino N, Marine J C, Takahashi Y, Muller M, Martial J A, Cleveland J L (2001). The ornithine decarboxylase gene is essential for cell survival during early murine development. Mol. Cell Biol. 21, 6549-6558.

Poulin R, Lu L, Ackermann B, Bey P, Pegg A E (1992). Mechanism of the irreversible inactivation of mouse ornithine decarboxylase by α-difluoromethylornithine. Characterization of sequences at the inhibitor and coenzyme binding sites. J. Biol. Chem. 267, 150-158.

Selesniemi K, Lee H J, Muhlhauser A, Tilly J L (2011). From the Cover: Prevention of maternal aging-associated oocyte aneuploidy and meiotic spindle defects in mice by dietary and genetic strategies. Proc. Natl. Acad. Sci. U.S.A 108, 12319-12324.

Sunkara P S, Wright D A, Nishioka K (1981). An essential role for putrescine biosynthesis during meiotic maturation of amphibian oocytes. Dev. Biol. 87, 351-355.

Tao, Y. and X. J. Liu. 2013. Deficiency of ovarian ornithine decarboxylase contributes to aging-related egg aneuploidy in mice. Aging Cell 12:42-49.

Whitney P A, Morris D R (1978). Polyamine auxotrophs of *Saccharomyces cerevisiae*. J. Bacteriol. 134, 214-220.

Wolstenholme J, Angell R R (2000). Maternal age and trisomy—a unifying mechanism of formation. Chromosoma 109, 435-438.

Younglai E V, Godeau F, Mester J, Baulieu E E (1980). Increased ornithine decarboxylase activity during meiotic maturation in *Xenopus laevis* oocytes. Biochem. Biophys. Res. Commun. 96, 1274-1281.

Zhou Y, Ma C, Karmouch J, Katbi H A, Liu X J (2009). Antiapoptotic role for ornithine decarboxylase during oocyte maturation. Mol. Cell Biol. 29, 1786-1795.

What is claimed is:

1. A method of reducing the risk of having an aneuploid pregnancy in a human female with reduced ovarian ornithine decarboxylase (ODC) activity level, the method comprising: administering putrescine to a peri-ovulatory human female.

2. The method according to claim 1 wherein the human female with reduced ovarian ODC activity level is a human female older than 32 years of age.

3. The method according to claim 1 wherein the putrescine is administered to the human female at about 0.02 g/kg to about 1 g/kg daily.

4. The method according to claims 1 wherein the putrescine is administered at least on the day of ovulation.

5. The method according to claim 4, wherein the putrescine is formulated for administration up to and including the day of ovulation.

6. The method according to claim 5, wherein the putrescine is administered for one week up to and including the day of ovulation.

7. The method according to claim 4, wherein the human female is an IVF patient and the putrescine is administered to the IVF patient for one week up to the morning of egg retrieval.

8. The method according to claim 4, wherein the putrescine is administered for 5-8 days up to and including the day of conception.

9. The method according to claim 1 wherein reducing the risk of having an aneuploid pregnancy comprises reducing the ovulation of aneuploid eggs and/or reducing the generation of aneuploid embryos.

10. The method according to claim wherein reducing the risk of having an aneuploid pregnancy: increases the probability that the human female will have a viable pregnancy, reduces the probability that the human female will have a child with a birth defect, or both, when compared to the probability when the human female is not administered the putrescine.

11. The method according to claim 7 wherein the human female with reduced ovarian ODC activity level is a human female older than 32 years of age.

12. The method according to claim 7 wherein the putrescine is administered to the human female at about 0.02 g/kg to about 1 g/kg daily.

13. The method according to claim 7 wherein reducing the risk of having an aneuploid pregnancy comprises reducing the ovulation of aneuploid eggs and/or reducing the generation of aneuploid embryos.

14. A method according to claim 7 wherein reducing the risk of having an aneuploid pregnancy: increases the probability that the human female will have a viable pregnancy, reduces the probability that the human female will have a child with a birth defect, or both, when compared to the probability when the human female is not administered the putrescine.

15. A method of reducing the risk of miscarriage in a human female with reduced ovarian ornithine decarboxylase (ODC) activity level, the method comprising:
   administering putrescine to a pen-ovulatory human female.

16. The method according to claim 13 wherein the human female is an IVF patient and the putrescine is administered to the IVF patient for one week up to the morning of egg retrieval.

17. The method according to claim 16 wherein the human female with reduced ovarian ODC activity level is a human female older than 32 years of age.

18. The method according to claim 16 wherein the putrescine is administered to the human female at about 0.02 g/kg to about 1 g/kg daily.

19. The method according to claim 15 wherein the human female with reduced ovarian ODC activity level is a human female older than 32 years of age.

20. The method according to claim 15 wherein the putrescine is administered to the human female at about 0.02 g/kg to about 1 g/kg daily.

* * * * *